(12) United States Patent
Meir et al.

(10) Patent No.: US 9,790,489 B2
(45) Date of Patent: Oct. 17, 2017

(54) METHOD FOR PERFORMING GENETIC MODIFICATION UNDER A DRUG-FREE ENVIRONMENT AND COMPONENTS THEREOF

(75) Inventors: Yaa-Jyuhn James Meir, Tao-Yuan (TW); Chiung-Yuan Sareina Wu, Martinez, GA (US); Herng-Shing Yang, Martinez, GA (US)

(73) Assignee: CHANG GUNG UNIVERSITY, Kwei-Shan Tao-Yuan (TW)

( * ) Notice: Subject to any disclaimer, the term of this patent is extended or adjusted under 35 U.S.C. 154(b) by 985 days.

(21) Appl. No.: 12/588,708

(22) Filed: Oct. 26, 2009

(65) Prior Publication Data

US 2011/0099649 A1   Apr. 28, 2011

(51) Int. Cl.
 *C12N 15/10* (2006.01)
 *C12N 15/90* (2006.01)

(52) U.S. Cl.
 CPC ..... *C12N 15/1086* (2013.01); *C12N 15/1051* (2013.01); *C12N 15/1065* (2013.01); *C12N 15/90* (2013.01); *C12N 2800/40* (2013.01); *C12N 2800/90* (2013.01); *C12N 2840/44* (2013.01)

(58) Field of Classification Search
 CPC .......... C12N 15/1086; C12N 15/1051
 See application file for complete search history.

(56) References Cited

U.S. PATENT DOCUMENTS

2004/0117865 A1* 6/2004 Takeda et al. ................... 800/14
2009/0042297 A1* 2/2009 George et al. ................ 435/455

OTHER PUBLICATIONS

Sumitani et al (Insect Biochemistry and Molecular Biology 33: 449-458, 2003).*
Ding et al (Cell 122: 473-483, 2005).*
Schnütgen et al (Nucleic Acids Res. Nov. 2008; 36(20): e133).*
Scott et al (Nat Methods 4(4): 323-6. Epub Mar. 18, 2007).*
Fu et al (Genome, 48(4):722-30, 2005).*
Wilson et al (Mol Ther, 15(1): 139-45, 2007).*

* cited by examiner

*Primary Examiner* — Anoop Singh
*Assistant Examiner* — Magdalene Sgagias
(74) *Attorney, Agent, or Firm* — Bacon & Thomas, PLLC

(57) ABSTRACT

The present invention provides a method and components thereof of performing genetic modification under a drug-free environment. The method comprises the steps of generating a trapped mammalian cell library by trapper constructs (including the element of piggyBac terminal inverted repeats (TIRs)), reporter constructs, and helper constructs (including a sequence of an internal ribosomal entry site (IRES)). The present art allows: (1) to target & identify the silenced loci; (2) to separate genes with low-level expression at certain differentiation stages; (3) to evaluate the efficiency of gene targeting in the silent or repressed loci. The present invention avoids the biased gene targeting observed in the prior arts, and eliminates the needs of introducing antibiotic genes into the host genome which may lead to a potential threat of drifting antibiotic resistant genes into environment.

4 Claims, 7 Drawing Sheets

SEQUENCE LISTING

<160> NUMBER OF SEQ ID NOS: 3

<210> SEQ ID NO 1
<211> LENGTH: 11504
<212> TYPE: DNA
<213> ORGANISM: Artificial Sequence
<220> FEATURE:
<223> OTHER INFORMATION: Trapper construct of piggyBac transposon

<400> SEQUENCE: 1

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggcaatt | catgggaaga | ggaaccgaaa | gtatgttttt | cagatgttct | 660 |
| ttctcagaaa | taggagtttg | cggaggttgg | agtgtgtgtt | gtaggacacg | aaccccaggg | 720 |
| tggaggagac | tggaggacag | agccctcttt | cccagggagg | aaggaggag | agtttgagat | 780 |
| ccgctccgga | agtcggggtt | caggtttgag | caggccaggc | ctctcccgtg | gtctcgccct | 840 |
| cttgtcctag | aagcctcact | ggccaggtgt | aagccaggtc | gtgggtgccg | agccctgctc | 900 |
| cctcatcctc | agcatggatg | tgaagaggac | tgtatggcgt | gcgggtgtgt | gtgaccgtgg | 960 |
| gtacacttaa | acaccgggt | tttggatctg | cactgtcccg | gatgtcctct | ggtgctcaaa | 1020 |
| gaccctttg | ggtttgccct | ttggtaagag | cgccgggatc | tacttgtctg | gaggccaggg | 1080 |
| agtcctcagc | cgaggcttgc | cgcccctgac | tgcactgcac | tgagtagtgg | atgggagagt | 1140 |
| ctggtaccgc | actgccggtt | tcctccacca | tccccgcagc | gcagggcagt | gcattccgtc | 1200 |
| ctggctgcga | aggggatgg | tcgggccttc | tccagcctct | tccgcttcta | gcgaaggggc | 1260 |
| cttgatggaa | gggcccgcat | gtctccaaag | ttgattcatg | cttcttgcac | agagaaagac | 1320 |
| cagaaagaag | gtctcaagtt | ttagccggta | gcccggatgg | ccttttcctg | cacggcacca | 1380 |
| tatgaacctt | gtgaccctga | ctttgagacc | cctctaaccc | aaggcccta | ccactttacc | 1440 |
| cttccctttt | gaaggctttc | ccacaccacc | ctccacactt | cccaaacac | tgccaactat | 1500 |
| gtaggaggaa | ggggttggga | ctaacagaag | aacccgttgt | ggggaagctg | ttgggagggt | 1560 |
| cactttatgt | tcttgcccaa | ggtcagttgg | gtggcctgct | tctgatgagg | tggtcccaag | 1620 |
| gtctggggta | gaaggtgaga | gggacaggcc | accaaggtca | gccccccccc | cctatcccat | 1680 |
| aggagccagg | tccctctcct | ggacaggaag | actgaagggg | agatgccaga | gactcagtga | 1740 |
| agcctggggt | accctattgg | agtccttcaa | ggaaacaaac | ttggcctcac | caggcctcag | 1800 |
| ccttggctcc | tcctgggaac | tctactgccc | ttggatccc | ttgtagttgt | gggttacata | 1860 |
| ggaaggggac | ggattcccct | tgactggcta | gcctactctt | tcttcagtc | ttctccatct | 1920 |
| cctctcaccg | ttctctcgac | cctttcccta | ggatagactt | ggaaaagat | aaggggagaa | 1980 |
| aaacaaatgc | aaacgaggcc | agaaagattt | tggctgggca | ttccttccgc | tagcttttat | 2040 |

```
tgggatcccc tagtttgtga taggccttt  agctacatct gccaatccat ctcattttca    2100
cacacacaca caccactttc cttctggtca gtgggcacat gtccagcctc aagtttatat    2160
caccaccccc aatgcccaac acttgtatgg ccttggcggg tcatccccc  ccccacccc     2220
agtatctgca acctcaagct agcttgggtg cgttggttgt ggataagtag ctagactcca    2280
gcaaccagta acctctgccc tttctcctcc atgacaacca ggtcccaggt cccgaaaacc    2340
tgagtaggta aagatctcaa ttggggcccc tatagtgtca cctaaataat tccgcccccc    2400
cctctccctc ccccccccct aacgttactg gccgaagccg cttggaataa ggccggtgtg    2460
cgtttgtcta tatgttattt tccaccatat tgccgtcttt tggcaatgtg agggcccgga    2520
aacctggccc tgtcttcttg acgagcattc ctaggggtct ttccctctc  gccaaggaa     2580
tgcaaggtct gttgaatgtc gtgaaggaag cagttcctct ggaagcttct tgaagacaaa    2640
caacgtctgt agcgacccct tgcaggcagc ggaacccccc acctggcgac aggtgcctct    2700
gcggccaaaa gccacgtgta taagatacac ctgcaaaggc ggcacaaccc cagtgccacg    2760
ttgtgagttg atagttgtg  gaaagagtca atggctctc  ctcaagcgta ttcaacaagg    2820
ggctgaagga tgcccagaag gtaccccatt gtatgggatc tgatctgggg cctcggtgca    2880
catgctttac atgtgtttag tcgaggttaa aaaaacgtct aggcccccg  aaccacgggg    2940
acgtggtttt cctttgaaaa acacgatgat aaatatggaat tcaccatgac cccccccaag    3000
aagaagcgca aggtggagga cggaatgaag ctactgtctt ctatcgaaca agcatgcgat    3060
atttgccgac ttaaaaagct caagtgctcc aaagaaaaac cgaagtgcgc caagtgtctg    3120
aagaacaact gggagtgtcg ctactctccc aaaaccaaaa ggtctccgct gactagggca    3180
catctgacag aagtggaatc aaggctagaa agactggaac agctatttct actgattttt    3240
cctcgagaag accttgacat gattttgaaa atggattctt tacaggatat aaaagcattg    3300
ttaacaggat tatttgtaca agataatgtg aataaagatg ccgtcacaga tagattggct    3360
tcagtggaga ctgatatgcc tctaacattg agacagcata gaataagtgc gacatcatca    3420
tcggaagaga gtagtaacaa aggtcaaaga cagttgactg tatcgattga ctcggcagct    3480
catcatgata actccacaat tccgttggat tttatgccca gggatgctct tcatggattt    3540
gattggtctg aagaggatga catgtcggat ggcttgccct tcctgaaaac ggaccccaac    3600
aataatgggt tctttggcga cggttctctc ttatgtattc ttcgatctat tggctttaaa    3660
ccggaaaatt acacgaactc taacgttaac aggctcccga ccatgattac ggatagatac    3720
acgttggctt ctagatccac aacatcccgt ttacttcaaa gttatctcaa taatttcac     3780
ccctactgcc ctatcgtgca ctcaccgacg ctaatgatgt tgtataataa ccagattgaa    3840
atcgcgtcga aggatcaatg gcaaatcctt tttaactgca tattagccat ggagcctgg     3900
tgtatagagg gggaatctac tgatatagat gttttttact atcaaaatgc taaatctcat    3960
ttgacgagca aggtcttcga gtcaggttcc ataattttgg tgacagccct acatcttctg    4020
tcgcgatata cacagtggag gcagaaaaca aatactagct ataattttca cagcttttcc    4080
ataagaatgg ccatatcatt gggcttgaat agggacctcc cctcgtcctt cagtgatagc    4140
agcattctgg aacaaagacg ccgaatttgg tggtctgtct actcttggga gatccaattg    4200
tccctgcttt atggtcgatc catccagctt tctcagaata caatctcctt cccttcttct    4260
gtcgacgatg tgcagcgtac cacaacaggt cccaccatat atcatggcat cattgaaaca    4320
gcaaggctct tacaagtttt cacaaaaatc tatgaactag acaaaacagt aactgcgaa     4380
```

```
aaaagtccta tatgtgcaaa aaaatgcttg atgatttgta atgagattga ggaggtttcg    4440
agacaggcac caaagttttt acaaatggat atttccacca ccgctctaac caatttgttg    4500
aaggaacacc cttggctatc ctttacaaga ttcgaactga agtggaaaca gttgtctctt    4560
atcatttatg tattaagaga ttttttcact aattttaccc agaaaaagtc acaactagaa    4620
caggatcaaa atgatcatca aagttatgaa gttaaacgat gctccatcat gttaagcgat    4680
gcagcacaaa gaactgttat gtctgtaagt agctatatgg acaatcataa tgtcacccca    4740
tattttgcct ggaattgttc ttattacttg ttcaatgcag tcctagtacc cataaagact    4800
ctactctcaa actcaaaatc gaatgctgag aataacgaga ccgcacaatt attacaacaa    4860
attaacactg ttctgatgct attaaaaaaa ctggccactt ttaaaatcca gacttgtgaa    4920
aaatacattc aagtactgga agaggtatgt gcgccgtttc tgttatcaca gtgtgcaatc    4980
ccattaccgc atatcagtta taacaatagt aatggtagcg ccattaaaaa tattgtcggt    5040
tctgcaacta tcgcccaata ccctactctt ccggaggaaa atgtcaacaa tatcagtgtt    5100
aaatatgttt ctcctggctc agtagggcct tcacctgtgc cattgaaatc aggagcaagt    5160
ttcagtgatc tagtcaagct gttatctaac cgtccaccct ctcgtaactc tccagtgaca    5220
ataccaagaa gcacaccttc gcatcgctca gtcacgcctt ttctagggca acagcaacag    5280
ctgcaatcat tagtgccact gaccccgtct gctttgtttg gtggcgccaa ttttaatcaa    5340
agtgggaata ttgctgatag ctcattgtcc ttcactttca ctaacagtag caacggtccg    5400
aacctcataa caactcaaac aaattctcaa gcgctttcac aaccaattgc ctcctctaac    5460
gttcatgata acttcatgaa taatgaaatc acggctagta aaattgatga tggtaataat    5520
tcaaaaccac tgtcacctgg ttggacggac caaactgcgt ataacgcgtt tggaatcact    5580
acagggatgt ttaataccac tacaatggat gatgtatata actatctatt cgatgatgaa    5640 gatacccccac caaacccaaa aaaagagtaa aatgaatcgt agatactgaa aaaccccgca    5700
agttcacttc aactgtgcat cgtgcaccat ctcaatttct ttcatttata catcgttttg    5760
ccttctttta tgtaactata ctcctctaag tttcaatctt ggccatgtaa cctctgatct    5820
atagaatttt ttaaatgact agaattaatg cccatctttt ttttggacct aaattcttca    5880
tgaaaatata ttacgagggc ttattcagaa gcttatcgat accgtcgacc tcgaggggg    5940 gcccgtttaa acccgctgat cagcctcgac tgtgccttct agttgccagc catctgttgt    6000 ttgccccctcc cccgtgcctt ccttgaccct ggaaggtgcc actcccactg tccttttccta    6060 ataaaatgag gaaattgcat cgcattgtct gagtaggtgt cattctattc tggggggtgg    6120
ggtggggcag gacagcaagg gggaggattg ggaagacaat agcaggcatg ctggggatgc    6180
ggtgggctct atggcttctg aggcggaaag aaccagctgg ggctctaggg ggtatcccca    6240
cgcgccctgt agcggcgcat taagcgcggc gggtgtggtg gttacgcgca gcgtgaccgc    6300
tacacttgcc agcgccctag cgcccgctcc tttcgctttc ttcccttcct ttctcgccac    6360
gttcgccggt gtccgttaca taacttacgg taaatggccc gcctggctga ccgcccaacg    6420
acccccgccc attgacgtca ataatgacgt atgttcccat agtaacgcca atagggactt    6480
tccattgacg tcaatgggtg gagtatttac ggtaaactgc ccacttggca gtacatcaag    6540
tgtatcatat gccaagtacg ccccctattg acgtcaatga cggtaaatgg cccgcctggc    6600
attatgccca gtacatgacc ttatgggact ttcctacttg gcagtacatc tacgtattag    6660
tcatcgctat taccatggtg atgcggtttt ggcagtacat caatgggcgt ggatagcggt    6720
ttgactcacg gggatttcca agtctccacc ccattgacgt caatgggagt ttgttttggc    6780
```

-continued

```
accaaaatca acgggacttt ccaaaatgtc gtaacaactc cgccccattg acgcaaatgg    6840
gcggtaggcg tgtacggtgg gaggtctata taagcagagc tcgtttagtg aaccgtcaga    6900
tcgcctggag acgccatcca cgctgttttg acctccatag aagacaccgg gaccgatcca    6960
gcctccgcgg actagtccgg gaacggtgca ttggaacgga ccgtgttgac aattaatcat    7020
cggcatagta tatcggcata gtataatacg acaaggtgag gaactaaacc atggctagca    7080
tgattgaaca agatggattg cacgcaggtt ctccggccgc ttgggtggag aggctattcg    7140
gctatgactg ggcacaacag acaatcggct gctctgatgc cgccgtgttc cggctgtcag    7200
cgcaggggcg cccggttctt tttgtcaaga ccgacctgtc cggtgccctg aatgaactgc    7260
aagacgaggc agcgcggcta tcgtggctgg ccacgacggg cgttccttgc gcagctgtgc    7320
tcgacgttgt cactgaagcg ggaagggact ggctgctatt gggcgaagtg ccggggcagg    7380
atctcctgtc atctcacctt gctcctgccg agaaagtatc catcatggct gatgcaatgc    7440
ggcggctgca tacgcttgat ccggctacct gcccattcga ccaccaagcg aaacatcgca    7500
tcgagcgagc acgtactcgg atggaagccg gtcttgtcga tcaggatgat ctggacgaag    7560
agcatcaggg gctcgcgcca gccgaactgt tcgccaggct caaggcgagc atgcccgacg    7620
gcgaggatct cgtcgtgacc catggcgatg cctgcttgcc gaatatcatg gtggaaaatg    7680
gccgcttttc tggattcatc gactgtggcc ggctgggtgt ggcggaccgc tatcaggaca    7740
tagcgttggc tacccgtgat attgctgaag agcttggcgg cgaatgggct gaccgcttcc    7800
tcgtgcttta cggtatcgcc gctcccgatt cgcagcgcat cgccttctat cgccttcttg    7860
acgagttctt ctgagggccc gtttaaaccc gctgatcagc ctcgactgtg ccttctagtt    7920
gccagccatc tgttgtttgc ccctcccccg tgccttcctt gaccctggaa ggtgccactc    7980
ccactgtcct ttcctaataa aatgaggaaa ttgcatcgca ttgtctgagt aggtgtcatt    8040
ctattctggg gggtggggtg gggcaggaca gcaaggggga ggattgggaa gacaatagca    8100
ggcatgctgg ggatgcggtg ggctctatgg cttctgaggc ggaaagaacc agcatgtgag    8160
caaaaggcca gcaaaggcca aggaaccgta aaaaggccgc gttgctggcg ttttttccata    8220
ggctccgccc cctgacgag catcacaaaa atcgacgctc aagtcagagg tggcgaaacc    8280
cgacaggact ataaagatac caggcgtttc ccctggaag ctccctcgtg cgctctcctg    8340
ttccgacct gccgcttacc ggatacctgt ccgcctttct cccttcggga agcgtggcgc    8400
tttctcatag ctcacgctgt aggtatctca gttcggtgta ggtcgttcgc tccaagctgg    8460
gctgtgtgca cgaaccccc gttcagcccg accgctgcgc cttatccggt aactatcgtc    8520
ttgagtccaa cccggtaaga cacgacttat cgccactggc agcagccact ggtaacagga    8580
ttagcagagc gaggtatgta ggcggtgcta cagagttctt gaagtggtgg cctaactacg    8640
gctacactag aagaacagta tttggtatct gcgctctgct gaagccagtt accttcggaa    8700
aaagagttgg tagctcttga tccggcaaac aaaccaccgc tggtagcggt ggtttttttg    8760
tttgcaagca gcagattacg cgcagaaaaa aaggatctca agaagatcct ttgatctttt    8820
ctacggggtc tgacgctcag tggaacgaaa actcacgtta agggattttg gtcaatttaa    8880
ataccggctt tccccgtcaa gctctaaatc ggggggctccc tttagggttc cgatttagtg    8940
ctttacggca cctcgacccc aaaaaacttg attagggtga tggttcacgt agtgggccat    9000
cgccctgata gacggttttt cgccctttga cgttggagtc cacgttcttt aatagtggac    9060
tcttgttcca aactggaaca acactcaacc ctatctcggt ctattctttt gatttataag    9120
```

```
ggattttgcc gatttcggcc tattggttaa aaaatgagct gatttaacaa aaatttaacg    9180
cgaattaatt ctgtggaatg tgtgtcagtt agggtgtgga aagtcccag gctccccagc      9240
aggcagaagt atgcaaagca cattctagtt gtggtttgtc caaactcatc aatgtatctt    9300
atcatgtctg tataccgtcg acctctagct agagcttggc gtaatcatgg tcatagctgt    9360
ttcctgtgtg aaattgttat ccgctcacaa ttccacacaa catacgagcc ggaagcataa    9420
agtgtaaagc ctggggtgcc taatgagtga gctaactcac attaattgcg ttgcgctcac    9480
tgcccgcttt ccagtcggga aacctgtcgt gccagctgca ttaatgaatc ggccaacgcg    9540
cggggagagg cggtttgcgt attgggcgct cttccgcttc ctcgctcact gactcgctgc    9600
gctcggtcgt tcggctgcgg cgagcggtat cagctcactc aaaggcggta atacggttat    9660
ccacagaatc aggggataac gcaggaaaga acatgtgagc aaaaggccag caaaaggcca    9720
ggaaccgtaa aaaggccgcg ttgctggcgt ttttccatag gctccgcccc cctgacgagc    9780
atcacaaaaa tcgacgctca agtcagaggt ggcgaaaccc gacaggacta taaagatacc    9840
aggcgtttcc ccctggaagc tccctcgtgc gctctcctgt tccgaccctg ccgcttaccg    9900
gatacctgtc cgcctttctc ccttcgggaa gcgtggcgct ttctcatagc tcacgctgta    9960
ggtatctcag ttcggtgtag tcgttcgct ccaagctggg ctgtgtgcac gaaccccccg     10020
ttcagcccga ccgctgcgcc ttatccggta actatcgtct tgagtccaac ccggtaagac    10080
acgacttatc gccactggca gcagccactg gtaacaggat tagcagagcg aggtatgtag    10140
gcggtgctac agagttcttg aagtggtggc ctaactacgg ctacactaga agaacagtat    10200
ttggtatctg cgctctgctg aagccagtta ccttcggaaa aagagttggt agctcttgat    10260
ccggcaaaca aaccaccgct ggtagcggtt ttttgtttg caagcagcag attacgcgca      10320
gaaaaaaagg atctcaagaa gatcctttga tcttttctac ggggtctgac gctcagtgga    10380
acgaaaactc acgttaaggg attttggtca tgagattatc aaaaaggatc ttcacctaga    10440
tccttttaaa ttaaaaatga agttttaaat caatctaaag tatatatgag taaacttggt    10500
ctgacagtta ccaatgctta atcagtgagg cacctatctc agcgatctgt ctatttcgtt    10560
catccatagt tgcctgactc cccgtcgtgt agataactac gatacgggag gcttaccat     10620
ctggccccag tgctgcaatg ataccgcgag acccacgctc accggctcca gatttatcag    10680
caataaacca gccagccgga agggccgagc gcagaagtgg tcctgcaact ttatccgcct    10740
ccatccagtc tattaattgt tgccgggaag ctagagtaag tagttcgcca gttaatagtt    10800
tgcgcaacgt tgttgccatt gctacaggca tcgtggtgtc acgctcgtcg tttggtatgg    10860
cttcattcag ctccggttcc caacgatcaa ggcgagttac atgatccccc atgttgtgca    10920
aaaaagcggt tagctccttc ggtcctccga tcgttgtcag aagtaagttg gccgcagtgt    10980
tatcactcat ggttatggca gcactgcata attctcttac tgtcatgcca tccgtaagat    11040
gcttttctgt gactggtgag tactcaacca agtcattctg agaatagtgt atgcggcgac    11100
cgagttgctc ttgcccggcg tcaatacggg ataataccgc gccacatagc agaactttaa    11160
aagtgctcat cattggaaaa cgttcttcgg ggcgaaaact ctcaaggatc ttaccgctgt    11220
tgagatccag ttcgatgtaa cccactcgtg cacccaactg atcttcagca tcttttactt    11280
tcaccagcgt ttctgggtga gcaaaaacag gaaggcaaaa tgccgcaaaa aagggaataa    11340
gggcgacacg gaaatgttga atactcatac tcttcctttt tcaatattat tgaagcattt    11400
atcagggtta ttgtctcatg agcggataca tatttgaatg tatttagaaa aataaacaaa    11460
tagggggttcc gcgcacattt ccccgaaaag tgccacctga cgtc                    11504
```

```
<210> SEQ ID NO 2
<211> LENGTH: 7233
<212> TYPE: DNA
<213> ORGANISM: Artificial Sequence
<220> FEATURE:
<223> OTHER INFORMATION: Helper construct of piggyBac transposon

<400> SEQUENCE: 2
gagttcgagc ttgcatgcct gcaggtcgtt acataactta cggtaaatgg cccgcctggc      60
tgaccgccca acgacccccg cccattgacg tcaataatga cgtatgttcc catagtaacg     120
ccaataggga ctttccattg acgtcaatgg gtggagtatt tacggtaaac tgcccacttg     180
gcagtacatc aagtgtatca tatgccaagt acgcccccta ttgacgtcaa tgacggtaaa     240
tggcccgcct ggcattatgc ccagtacatg accttatggg actttcctac ttggcagtac     300
atctacgtat tagtcatcgc tattaccatg gtgatgcggt tttggcagta catcaatggg     360
cgtggatagc ggtttgactc acggggattt ccaagtctcc accccattga cgtcaatggg     420
agtttgtttt ggcaccaaaa tcaacgggac tttccaaaat gtcgtaacaa ctccgcccca     480
ttgacgcaaa tgggcggtag gcgtgtacgg tgggaggtct atataagcag agctcgttta     540
gtgaaccgtc agatcgcctg gagacgccat ccacgctgtt tgacctccat agaagacac      600
cgggaccgat ccagcctccg gactctagag gatccggtac tagaggaact gaaaaaccag     660
aaagttaact ggtaagttta gtcttttttgt cttttatttc aggtcccgga tccggtggtg     720
gtgcaaatca agaactgct cctcagtgga tgttgccttt acttctaggc ctgtacggaa      780
gtgttacttc tgctctaaaa gctgcggaat tgtacccgcg gcccaccat ggcatcaatg       840
cagaagctga tctcagagga ggacctgctt atggccatgg aggcccgaat ctgcagatg       900
gataaaatgg gtagttcttt agacgatgag catatcctct ctgctcttct gcaaagcgat     960
gacgagcttg ttggtgagga ttctgacagt gaaatatcag atcacgtaag tgaagatgac    1020
gtccagagcg atacagaaga agcgtttata gatgaggtac atgaagtgca gccaacgtca    1080
agcggtagtg aaatattaga cgaacaaaat gttattgaac aaccaggttc ttcattggct    1140
tctaacagaa tcttgacctt gccacagagg actattagag gtaagaataa acattgttgg    1200
tcaacttcaa agtccacgag gcgtagccga gtctctgcac tgaacattgt cagatctcaa    1260
agaggtccga cgcgtatgtg ccgcaatata tatgacccac ttttatgctt caaactattt    1320
tttactgatg agataatttc ggaaattgta aaatggacaa atgctgagat atcattgaaa    1380
cgtcgggaat ctatgacagg tgctacattt cgtgacacga atgaagatga atctatgct     1440
ttctttggta ttctggtaat gacagcagtg agaaaagata atcacatgtc cacagatgac    1500
ctctttgatc gatctttgtc aatggtgtac gtctctgtaa tgagtcgtga tcgttttgat    1560
tttttgatac gatgtcttag aatggatgac aaaagtatac ggcccacact tcgagaaaac    1620
gatgtattta ctcctgttag aaaaatatgg gatctctta tccatcagtg catacaaaat    1680
tacactccag gggctcattt gaccatagat gaacagttac ttggttttag aggacggtgt    1740
ccgtttagga tgtatatccc aaacaagcca gtaagtatg gaataaaaat cctcatgatg    1800
tgtgacagtg gtacgaagta tatgataaat ggaatgcctt atttgggaag aggaacacag    1860
accaacggag taccactcgg tgaatactac gtgaaggagt tatcaaagcc tgtgcacggt    1920
agttgtcgta atattacgtg tgacaattgg ttcacctcaa tccctttggc aaaaaactta    1980
ctacaagaac cgtataagtt aaccattgtg ggaaccgtgc gatcaaacaa acgcgagata    2040
```

```
ccggaagtac tgaaaaacag tcgctccagg ccagtgggaa catcgatgtt ttgttttgac    2100
ggacccctta ctctcgtctc atataaaccg aagccagcta agatggtata cttattatca    2160
tcttgtgatg aggatgcttc tatcaacgaa agtaccggta aaccgcaaat ggttatgtat    2220
tataatcaaa ctaaaggcgg agtggacacg ctagaccaaa tgtgttctgt gatgacctgc    2280
agtaggaaga cgaataggtg gcctatggca ttattgtacg gaatgataaa cattgcctgc    2340
ataaattctt ttattatata cagccataat gtcagtagca agggagaaaa ggtccaaagt    2400
cgcaaaaaat ttatgagaaa cctttacatg agcctgacgt catcgtttat gcgtaagcgt    2460
ttagaagctc ctactttgaa gagatatttg cgcgataata tctctaatat tttgccaaat    2520
gaagtgcctg gtacatcaga tgacagtact gaagagccag taatgaaaaa acgtacttac    2580
tgtacttact gcccctctaa aataaggcga aaggcaaatg catcgtgcaa aaaatgcaaa    2640
aaagttattt gtcgagagca taatattgat atgtgccaaa gttgtttctg actgactaat    2700
aagtataatt tgtttctatt atgtataagt taagctaatt aggatcatcc agcacagtgg    2760
cggccgccgc ggcgtacgag gcctgcatgc tccggacctg caggttcgaa gtcgacagat    2820
ctcaattggg gcccctatag tgtcacctaa ataattccgc ccccccctct ccctccccc    2880 cccctaacgt tactggccga agccgcttgg aataaggccg gtgtgcgttt gtctatatgt    2940 tatttttccac catattgccg tcttttggca atgtgagggc ccggaaacct ggccctgtct    3000
tcttgacgag cattcctagg ggtctttccc ctctcgccaa aggaatgcaa ggtctgttga    3060
atgtcgtgaa ggaagcagtt cctctggaag cttcttgaag acaaacaacg tctgtagcga    3120 cccctttgcag gcagcggaac cccccacctg gcgacaggtg cctctgcggc caaaagccac    3180
gtgtataaga tacacctgca aaggcggcac aaccccagtg ccacgttgtg agttggatag    3240
ttgtggaaag agtcaaatgg ctctcctcaa gcgtattcaa caaggggctg aaggatgccc    3300
agaaggtacc ccattgtatg ggatctgatc tggggcctcg gtgcacatgc tttacatgtg    3360
tttagtcgag gttaaaaaaa cgtctaggcc ccccgaacca ggggacgtg gttttccttt     3420 gaaaaacacg atgataatat ggccacaacc atggtgagca agggcgagga gctgttcacc    3480
ggggtggtgc ccatcctggt cgagctggac ggcgacgtaa acggccacaa gttcagcgtg    3540
tccggcgagg gcgagggcga tgccacctac ggcaagctga ccctgaagtt catctgcacc    3600
accggcaagc tgcccgtgcc ctggcccacc ctcgtgacca ccctgaccta cggcgtgcag    3660
tgcttcagcc gctaccccga ccacatgaag cagcacgact tcttcaagtc cgccatgccc    3720
gaaggctacg tccaggagcg caccatcttc ttcaaggacg acggcaacta caagacccgc    3780
gccgaggtga agttcgaggg cgacaccctg gtgaaccgca tcgagctgaa gggcatcgac    3840
ttcaaggagg acggcaacat cctggggcac aagctggagt acaactacaa cagccacaac    3900
gtctatatca tggccgacaa gcagaagaac ggcatcaagg tgaacttcaa gatccgccac    3960
aacatcgagg acggcagcgt gcagctcgcc gaccactacc agcagaacac ccccatcggc    4020
gacggccccg tgctgctgcc cgacaaccac tacctgagca cccagtccgc cctgagcaaa    4080
gaccccaacg agaagcgcga tcacatggtc ctgctggagt tcgtgaccgc cgccgggatc    4140
actctcggca tggacgagct gtacaagtaa agcggcccga taaataaaa gattttattt    4200 agtctccaga aaagggggg aatgaaagac cccacctgta ggtttggcaa gctagcttaa    4260
gtaacgccat tttgcaaggc atggaaaata cataactgag aatagagaag ttcagatcaa    4320
ggttaggaac agagagacag cagaatatgg gccaaacagg atggccgcgg ggatccagac    4380
atgataagat acattgatga gtttggacaa accacaacta gaatgcagtg aaaaaaatgc    4440
```

```
tttatttgtg aaatttgtga tgctattgct ttatttgtaa ccattataag ctgcaataaa    4500
caagttaaca acaacaattg cattcatttt atgtttcagg ttcaggggga ggtgtgggag    4560
gttttttcgg atcctctaga gtcgatctgc aggcatgcta gcttggcgta atcatggtca    4620
tagctgtttc ctgtgtgaaa ttgttatccg ctcacaattc cacacaacat acgagccgga    4680
agcataaagt gtaaagcctg ggtgcctaa tgagtgagct aactcacatt aattgcgttg    4740
cgctcactgc ccgctttcca gtcgggaaac ctgtcgtgcc agctgcatta atgaatcggc    4800
caacgcgcgg ggagaggcgg tttgcgtatt gggcgctctt ccgcttcctc gctcactgac    4860
tcgctgcgct cggtcgttcg gctgcggcga gcggtatcag ctcactcaaa ggcggtaata    4920
cggttatcca cagaatcagg ggataacgca ggaaagaaca tgtgagcaaa aggccagcaa    4980
aaggccagga accgtaaaaa ggccgcgttg ctggcgtttt tccataggct ccgcccccct    5040
gacgagcatc acaaaaatcg acgctcaagt cagaggtggc gaaacccgac aggactataa    5100
agataccagg cgtttccccc tggaagctcc ctcgtgcgct ctcctgttcc gaccctgccg    5160
cttaccggat acctgtccgc ctttctccct tcgggaagcg tggcgctttc tcatagctca    5220
cgctgtaggt atctcagttc ggtgtaggtc gttcgctcca agctgggctg tgtgcacgaa    5280
ccccccgttc agcccgaccg ctgcgcctta tccggtaact atcgtcttga gtccaacccg    5340
gtaagacacg acttatcgcc actggcagca gccactggta acaggattag cagagcgagg    5400
tatgtaggcg gtgctacaga gttcttgaag tggtggccta actacggcta cactagaagg    5460
acagtatttg gtatctgcgc tctgctgaag ccagttacct tcggaaaaag agttggtagc    5520
tcttgatccg gcaaacaaac caccgctggt agcggtggtt tttttgtttg caagcagcag    5580
attacgcgca gaaaaaaagg atctcaagaa gatcctttga tcttttctac ggggtctgac    5640
gctcagtgga acgaaaactc acgttaaggg attttggtca tgagattatc aaaaaggatc    5700
ttcacctaga tccttttaaa ttaaaaatga agttttaaat caatctaaag tatatatgag    5760
taaacttggt ctgacagtta ccaatgctta atcagtgagg cacctatctc agcgatctgt    5820
ctatttcgtt catccatagt tgcctgactc ccgtcgtgt agataactac gatacgggag    5880
ggcttaccat ctggccccag tgctgcaatg ataccgcgag acccacgctc accggctcca    5940
gatttatcag caataaacca gccagccgga agggccgagc gcagaagtgg tcctgcaact    6000
ttatccgcct ccatccagtc tattaattgt tgccgggaag ctagagtaag tagttcgcca    6060
gttaatagtt tgcgcaacgt tgttgccatt gctacaggca tcgtggtgtc acgctcgtcg    6120
tttggtatgg cttcattcag ctccggttcc caacgatcaa ggcgagttac atgatccccc    6180
atgttgtgca aaaaagcggt tagctccttc ggtcctccga tcgttgtcag aagtaagttg    6240
gccgcagtgt tatcactcat ggttatggca gcactgcata attctcttac tgtcatgcca    6300
tccgtaagat gcttttctgt gactggtgag tactcaacca agtcattctg agaatagtgt    6360
atgcggcgac cgagttgctc ttgcccggcg tcaatacggg ataataccgc gccacatagc    6420
agaactttaa aagtgctcat cattggaaaa cgttcttcgg ggcgaaaact ctcaaggatc    6480
ttaccgctgt tgagatccag ttcgatgtaa cccactcgtg cacccaactg atcttcagca    6540
tcttttactt tcaccagcgt ttctgggtga gcaaaaacag gaaggcaaaa tgccgcaaaa    6600
aagggaataa gggcgacacg gaaatgttga atactcatac tcttcctttt tcaatattat    6660
tgaagcattt atcagggtta ttgtctcatg agcggataca tatttgaatg tatttagaaa    6720
aataaacaaa taggggttcc gcgcacattt ccccgaaaag tgccacctga cgtctaagaa    6780
```

| | |
|---|---:|
| accattatta tcatgacatt aacctataaa aataggcgta tcacgaggcc ctttcgtctc | 6840 |
| gcgcgtttcg gtgatgacgg tgaaaacctc tgacacatgc agctcccgga gacggtcaca | 6900 |
| gcttgtctgt aagcggatgc cgggagcaga caagcccgtc agggcgcgtc agcgggtgtt | 6960 |
| ggcgggtgtc ggggctggct taactatgcg gcatcagagc agattgtact gagagtgcac | 7020 |
| catatgcggt gtgaaatacc gcacagatgc gtaaggagaa ataccgcat caggcgccat | 7080 |
| tcgccattca ggctgcgcaa ctgttgggaa gggcgatcgg tgcgggcctc ttcgctatta | 7140 |
| cgccagctgg cgaaaggggg atgtgctgca aggcgattaa gttgggtaac gccagggttt | 7200 |
| tcccagtcac gacgttgtaa aacgacggcc agt | 7233 |

<210> SEQ ID NO 3
<211> LENGTH: 6054
<212> TYPE: DNA
<213> ORGANISM: Artificial Sequence
<220> FEATURE:
<223> OTHER INFORMATION: Report system of piggyBac transposon

<400> SEQUENCE: 3

| | |
|---|---:|
| gagttcgagc ttgcatgccg gatatccggc gctcgctaga gtctccgctc ggaggacagt | 60 |
| actccgctcg gaggacagta ctccgctcgg aggacagtac tccgctcgga ggacagtact | 120 |
| ccgctcggag gacagtactc cgacctgcag gcatggaagc ttggatcagg gtatataatg | 180 |
| ggagctcgtt tagtgaaccg tcagatcgcc tggagacgcc atccacgctg ttttgacctc | 240 |
| catagaagac accgggaccg atccagcctc cggactctag aggatccggt actagaggaa | 300 |
| ctgaaaaacc agaaagttaa ctggtaagtt tagtcttttt gtcttttatt tcaggtcccg | 360 |
| gatccggtgg tggtgcaaat caaagaactg ctcctcagtg gatgttgcct ttacttctag | 420 |
| gcctgtacga agtgttact tctgctctaa aagctgcgga attgtacccg cgggcccacc | 480 |
| atggcatcaa tgcagaagct gatctcagag gaggacctgc ttatggccat ggaggcccga | 540 |
| attcccatgc tagcaaagg agaagaactt ttcactggag ttgtcccaat tcttgttgaa | 600 |
| ttagatggtg atgttaatgg gcacaaattt tctgtcagtg gagagggtga aggtgatgct | 660 |
| acatacggaa agcttaccct taaatttatt tgcactactg gaaaactacc tgttccatgg | 720 |
| ccaacacttg tcactacttt ctcttatggt gttcaatgct tttcccgtta tccggatcat | 780 |
| atgaaacggc atgactttt caagagtgcc atgcccgaag gttatgtaca ggaacgcact | 840 |
| atatctttca agatgacgg aactacaag acgcgtgctg aagtcaagtt tgaaggtgat | 900 |
| acccttgtta atcgtatcga gttaaaaggt attgatttta aagaagatgg aaacattctc | 960 |
| ggacacaaac tcgagtacaa ctataactca cacaatgtat acatcacggc agacaaacaa | 1020 |
| aagaatggaa tcaaagctaa cttcaaaatt cgccacaaca ttgaagatgg atccgttcaa | 1080 |
| ctagcagacc attatcaaca aaatactcca attggcgatg gccctgtcct tttaccagac | 1140 |
| aaccattacc tgtcgacaca atctgcccct tcgaaagatc ccaacgaaaa gcgtgaccac | 1200 |
| atggtccttc ttgagtttgt aactgctgct gggattacac atggcatgga tgccaagttg | 1260 |
| accagtgccg ttccggtgct caccgcgcgc gacgtcgccg gagcggtcga gttctggacc | 1320 |
| gaccggctcg ggttctcccg ggacttcgtg gaggacgact cgccggtgt ggtccgggac | 1380 |
| gacgtgaccc tgttcatcag cgcggtccag gaccaggtgg tgccggacaa caccctggcc | 1440 |
| tgggtgtggg tgcgcggcct ggacgagctg tacgccgagt ggtcggaggt cgtgtccacg | 1500 |
| aacttccggg acgcctccgg ccggccatg accgagatcg cgagcagcc gtggggcggg | 1560 |
| gagttcgccc tgcgcgaccc ggccggcaac tgcgtgcact tcgtggccga ggagcaggac | 1620 |

```
tgataattga ctagagatct caattggggc ccctatagtg tcacctaaat aattccgccc    1680
cccctctcc ctccccccc cctaacgtta ctggccgaag ccgcttggaa taaggccggt     1740
gtgcgtttgt ctatatgtta ttttccacca tattgccgtc ttttggcaat gtgagggccc   1800
ggaaacctgg ccctgtcttc ttgacgagca ttcctagggg tctttcccct ctcgccaaag   1860
gaatgcaagg tctgttgaat gtcgtgaagg aagcagttcc tctggaagct tcttgaagac   1920
aaacaacgtc tgtagcgacc ctttgcaggc agcggaaccc cccacctggc gacaggtgcc   1980
tctgcggcca aaagccacgt gtataagata cacctgcaaa ggcggcacaa ccccagtgcc   2040
acgttgtgag ttggatagtt gtggaaagag tcaaatggct ctcctcaagc gtattcaaca   2100
aggggctgaa ggatgcccag aaggtacccc attgtatggg atctgatctg gggcctcggt   2160
gcacatgctt tacatgtgtt tagtcgaggt taaaaaaacg tctaggcccc ccgaaccacg   2220
gggacgtggt tttcctttga aaaacacgat gataatatgg ccacaaccat ggtgagcaag   2280
ggcgaggagc tgttcaccgg ggtggtgccc atcctggtcg agctggacgg cgacgtaaac   2340
ggccacaagt tcagcgtgtc cggcgagggc gagggcgatg ccacctacgg caagctgacc   2400
ctgaagttca tctgcaccac cggcaagctg cccgtgccct ggcccaccct cgtgaccacc   2460
ctgacctacg gcgtgcagtg cttcagccgc taccccgacc acatgaagca gcacgacttc   2520
ttcaagtccg ccatgcccga aggctacgtc caggagcgca ccatcttctt caaggacgac   2580
ggcaactaca agacccgcgc cgaggtgaag ttcgagggcg acaccctggt gaaccgcatc   2640
gagctgaagg gcatcgactt caaggaggac ggcaacatcc tggggcacaa gctggagtac   2700
aactacaaca gccacaacgt ctatatcatg gccgacaagc agaagaacgg catcaaggtg   2760
aacttcaaga tccgccacaa catcgaggac ggcagcgtgc agctcgccga ccactaccag   2820
cagaacaccc ccatcggcga cggccccgtg ctgctgcccg acaaccacta cctgagcacc   2880
cagtccgccc tgagcaaaga ccccaacgag aagcgcgatc acatggtcct gctggagttc   2940
gtgaccgccg ccgggatcac tctcggcatg gacgagctgt acaagtaaag cggccccgata   3000
aaataaaaga ttttatttag tctccagaaa aaggggggaa tgaaagaccc cacctgtagg   3060
tttggcaagc tagcttaagt aacgccattt tgcaaggcat ggaaaataca taactgagaa   3120
tagagaagtt cagatcaagg ttaggaacag agagacagca gaatatgggc caaacaggat   3180
cgcggccgcg gggatccaga catgataaga tacattgatg agtttggaca aaccacaact   3240
agaatgcagt gaaaaaaatg ctttatttgt gaaatttgtg atgctattgc tttatttgta   3300
accattataa gctgcaataa acaagttaac aacaacaatt gcattcattt tatgtttcag   3360
gttcaggggg aggtgtggga ggttttttcg gatcctctag agtcgatctg caggcatgct   3420
agcttggcgt aatcatggtc atagctgttt cctgtgtgaa attgttatcc gctcacaatt   3480
ccacacaaca tacgagccgg aagcataaag tgtaaagcct ggggtgccta atgagtgagc   3540
taactcacat taattgcgtt gcgctcactg cccgctttcc agtcgggaaa cctgtcgtgc   3600
cagctgcatt aatgaatcgg ccaacgcgcg gggagaggcg gtttgcgtat tgggcgctct   3660
tccgcttcct cgctcactga ctcgctgcgc tcggtcgttc ggctgcggcg agcggtatca   3720
gctcactcaa aggcggtaat acggttatcc acagaatcag gggataacgc aggaaagaac   3780
atgtgagcaa aaggccagca aaaggccagg aaccgtaaaa aggccgcgtt gctggcgttt   3840
ttccataggc tccgcccccc tgacgagcat cacaaaaatc gacgctcaag tcagaggtgg   3900
cgaaacccga caggactata aagataccag gcgtttcccc ctggaagctc cctcgtgcgc   3960
```

```
tctcctgttc cgaccctgcc gcttaccgga tacctgtccg cctttctccc ttcgggaagc    4020
gtggcgcttt ctcatagctc acgctgtagg tatctcagtt cggtgtaggt cgttcgctcc    4080
aagctgggct gtgtgcacga acccccgtt cagcccgacc gctgcgcctt atccggtaac     4140
tatcgtcttg agtccaaccc ggtaagacac gacttatcgc cactggcagc agccactggt    4200
aacaggatta gcagagcgag gtatgtaggc ggtgctacag agttcttgaa gtggtggcct    4260
aactacggct acactagaag gacagtattt ggtatctgcg ctctgctgaa gccagttacc    4320
ttcggaaaaa gagttggtag ctcttgatcc ggcaaacaaa ccaccgctgg tagcggtggt    4380 tttttttgttt gcaagcagca gattacgcgc agaaaaaaag gatctcaaga agatcctttg    4440 atctttcta cggggtctga cgctcagtgg aacgaaaact cacgttaagg gattttggtc     4500
atgagattat caaaaggat cttcacctag atccttttaa attaaaaatg aagttttaaa     4560
tcaatctaaa gtatatatga gtaaacttgg tctgacagtt accaatgctt aatcagtgag    4620
gcacctatct cagcgatctg tctatttcgt tcatccatag ttgcctgact ccccgtcgtg    4680
tagataacta cgatacggga gggcttacca tctggcccca gtgctgcaat gataccgcga    4740
gacccacgct caccggctcc agatttatca gcaataaacc agccagccgg aagggccgag    4800
cgcagaagtg gtcctgcaac tttatccgcc tccatccagt ctattaattg ttgccgggaa    4860
gctagagtaa gtagttcgcc agttaatagt ttgcgcaacg ttgttgccat tgctacaggc    4920
atcgtggtgt cacgctcgtc gtttggtatg gcttcattca gctccggttc caacgatca    4980 aggcgagtta catgatcccc catgttgtgc aaaaaagcgg ttagctcctt cggtcctccg    5040
atcgttgtca gaagtaagtt ggccgcagtg ttatcactca tggttatggc agcactgcat    5100
aattctctta ctgtcatgcc atccgtaaga tgcttttctg tgactggtga gtactcaacc    5160
aagtcattct gagaatagtg tatgcggcga ccgagttgct cttgcccggc gtcaatacgg    5220
gataataccg cgccacatag cagaacttta aaagtgctca tcattggaaa acgttcttcg    5280
gggcgaaaac tctcaaggat cttaccgctg ttgagatcca gttcgatgta acccactcgt    5340
gcacccaact gatcttcagc atcttttact ttcaccagcg tttctgggtg agcaaaaaca    5400
ggaaggcaaa atgccgcaaa aaagggaata agggcgacac ggaaatgttg aatactcata    5460
ctcttccttt ttcaatatta ttgaagcatt tatcagggtt attgtctcat gagcggatac    5520
atatttgaat gtatttagaa aaataaacaa ataggggttc cgcgcacatt tccccgaaaa    5580
gtgccacctg acgtctaaga aaccattatt atcatgacat taacctataa aaataggcgt    5640
atcacgaggc cctttcgtct cgcgcgtttc ggtgatgacg gtgaaaacct ctgacacatg    5700
cagctcccgg agacggtcac agcttgtctg taagcggatg ccgggagcag acaagcccgt    5760
cagggcgcgt cagcgggtgt tggcgggtgt cggggctggc ttaactatgc ggcatcagag    5820
cagattgtac tgagagtgca ccatatgcgg tgtgaaatac cgcacagatg cgtaaggaga    5880
aaataccgca tcaggcgcca ttcgccattc aggctgcgca actgttggga agggcgatcg    5940
gtgcgggcct cttcgctatt acgccagctg gcgaaagggg gatgtgctgc aaggcgatta    6000
agttgggtaa cgccagggtt ttcccagtca cgacgttgta aaacgacggc cagt          6054
```

METHOD FOR PERFORMING GENETIC MODIFICATION UNDER A DRUG-FREE ENVIRONMENT AND COMPONENTS THEREOF

BACKGROUND OF THE INVENTION

1. Field of the Invention

The present invention relates to a method for genetic manipulation in cell lines and organisms. More particularly, the invention relates to a method and components thereof for genetic manipulation without applying drug selections.

2. Description of the Prior Art

Since the recent completion of the human and mouse genome projects, genomic medicine becomes one of the fastest growing areas of biomedical research today. Enormous efforts are devoted to developing tools and technologies to decipher the human genetic code. However, how these three billion nucleotides of human genome carry out their multitudes of function is still largely remain unknown. The information of gene function is a prerequisite to delineate the therapeutic targets for disease diagnosis. Therefore, revealing the function of each gene and its role in the biological pathways will shed lights on the molecular mechanism of pathogenesis and in turn, leads to the development of effective therapeutic strategies. Due to the complexity of biological processes that form the basis of most diseases, the method of genome-wide genetic manipulation in model organisms is gaining a momentum in modern biological science.

Genetic alternation in established cell lines or the mouse genome has been the most frequently used strategy to dissect the structure and functions of genetic networks in mammals. Human and mouse gene share 99% of homology and many defects observed in knockout mice phenocopy those seen in human diseases. Hence, analyzing the defects in mice with a mutation in human gene counterparts is the most direct and cost-efficient approach for understanding human development, physiology, and diseases. Having been extensively used to extrapolate the observed physiological alternation from the mouse model to human disease, a mutant mouse library with individual mice carrying a mutation in one of all genes are highly demanded in both academic and biopharmaceutics.

Presently, approximate 66% of the protein coding genes in the mouse genome have been disrupted by random gene trap insertions (De-Zolt, et al., 2006). It is thought that only 60% of mouse genes can be effectively targeted by current gene traps technology. The limitation of gene trap technologies currently available is evident by the fact that after the percentage of genes trapped in the entire genome reaching the 60% limitation, the chance of trapping new genes in ES cell decreases exponentially. Thus, further trapping genes beyond the 60% limit will be non-effective and impractical since the chance of trapping new genes will drop down to zero long before completely trapping every single gene in the entire mouse genome (Skarnes, et al., 2004; 2005). The difficulty of trapping the remaining 40% of genes could be attributed to the inherited bias of retrovirus-mediated integration, developed by Lexicon Technology, that selectively targets genes actively expressed in ES cells (Scheridin, 1990). Alternatively, the structure of genes may also impede the accessibility of trapping cassette as revealed by trans-membrane domain containing proteins (De-Zolt, et al., 2006). Regardless, a major limitation of generating a gene trap library covering the entire genome is posed by the adverse effect of exclusively relying on drug selections to obtain targeted clones in all gene trap practices conducted so far.

Fraser discloses a "piggyBac constructs in vertebrates". The piggyBac transposon is disclosed herein as an extremely versatile helper-dependent vector for gene transfer and germ line transformation in a wide range of vertebrate species. PiggyBac mobility is demonstrated using an interplasmid transposition assay that consistently predicts the germ line transformation capabilities of this mobile element in several species. Both transfected COS-7 primate cells and injected zebrafish embryos supported the helper-dependent movement of tagged piggyBac element between plasmids in a cut-and-paste fashion.

Manfred (U.S. Pat. No. 5,922,601; July/1999) discloses a "High efficiency gene trap selection of regulated genetic loci". A gene trap construct for identification of genes whose activity is regulated upon a cellular transition event which comprises in downstream sequence: (i) a cassette having a functional splice acceptor, a translation stop sequence and an internal ribosome entry site and (ii) a promoterless protein coding sequence encoding at least one polypeptide providing positive and negative selection traits. A method for identification of genes whose activity is regulated upon a cellular transition event by introducing the gene trap construct into a cell and observing expression of the positive and/or negative selection traits before and after the transition event.

Zambrowicz (U.S. Pat. Nos. 6,436,707 and 6,080,576) discloses a "Vectors for gene mutagenesis and gene discovery". Novel vectors are described that incorporate, inter alia, a novel 3 gene trap cassette which can be used to efficiently trap and identify previously unknown cellular genes. Vectors incorporating the described 3 gene trap cassette find particular applications in gene discoveries and in the production of mutated cells and animals.

Ong discloses a "complementation trap". The methods and DNA constructs are provided for detection and manipulation of a targeted eukaryotic gene whose expression is restricted to certain tissues or specialized cell types. The methods include transforming a cell with a first indicator component under the control of a promoter selected for its restricted expression in a particular cell or tissue. The cell is also transformed with a gene trap vector encoding a second indicator component. The cell is allowed to differentiate to produce specialized cell or tissue which is monitored for expression of both the first and second indicator components, thereby detecting a gene into which the trap vector has integrated and is expressed in the same cell or tissue type as the selected promoter.

All of above prior arts using plasmid vectors, transposons, or viral vectors that can be performed in vertebrates and mammals to achieve genetic manipulations, such as the piggyBac transposon-mediated gene disruption and transgenesis, are exclusively mediated either by a drug (antibiotics) selection, reporter gene selection or specific phenotype (Tyrosinase I & II mutations) selection to manipulate cells or animals.

Applying the drug-mediated selection circumvents the difficulty of obtaining targeted clones as the efficiency of gene targeting is usually very low. It results in selectively targeting to actively expressed genes or genes in active chromosomal regions. Consequently, the prior arts in genetic modification are ineffective in manipulating genes that are silent or suppressed at the time of chromosomal modification.

Maintaining ES cell in a pluripotent status requires repression of some key genes crucial in determining the fate of ES cells as they differentiate toward a defined cell lineage. It has been recently shown that the mechanism of restricting expression of such genes in ES cell for maintaining ES cell pluripotency is governed by the polycomb repressive complex (PRC) (Boyer, et al., 2006; Bernstein, et al., 2006; Lee, et al., 2006). Since the PRC forms a higher order of chromatin complex structure in the promoter region of certain genes to assure their silent status, a drug-dependent gene trap approach is unlikely to be succeeded in harvesting ES clones trapped in such gene loci. This is a major obstacle encountered by all of gene trap technologies currently available. As silenced genes may constitute a large portion of the "untargetable" genes (about 40% of the entire mouse genes), there is a critical need in developing a high efficient drug-independent gene trap system to surpass this difficulty.

To circumvent the aforementioned difficulties, there remains a need for new methods to reach the goal of unbiased gene targeting without drug selection, particularly the methods that perform highly efficient chromosomal insertion and are able to target the silent regions on chromosomes.

SUMMARY OF THE INVENTION

According to a first aspect, the present invention provides a method and components thereof of performing genetic modification mediated by integrase-, recombinase- or transposase-like enzymes under a drug-free selection environment.

The objective of the present invention that provides a method for the drug-free selection during performing genetic engineering, and focuses on a method of targeting silent or repressed genes in mammalian cell lines or organisms under gene manipulation, gene disruption, gene insertion, or gene transgenesis. Moreover, the transgenic or gene disruption organisms comprise one or more insertions of the elements mediated by the transposase that is preferable the piggyBac-like transposon but not limited to the other enzymes for genetic modification.

Another object of the present invention provides a method for drug-free selection performing genetic manipulation, which comprises the steps of (a) generating an unbiased mouse stem cell gene-trap library including trapped clones targeting to the silenced gene loci; (b) evaluating the efficiency of targeting to silent or repressed genes; (c) engineering a reporter system to facilitate targeting genes with low level of gene expression.

A further object of the present invention provides a method to waive inevitable drug selection in targeting genes that are silenced or repressed during the process of genetic modification, such as gene disruption or gene transgenesis in cell lines including stem cells, somatic cells, and neuronal cells, and mammalian native or genetic modified organisms.

A further object of the present invention also provides a method and components thereof of performing genetic modification under the drug-free environment, which comprise the steps of (a) generating a trapped mammalian cell library by trapper constructs (including the element of piggyBac terminal inverted repeats (TIRs) and helper constructs (including a sequence of an internal ribosomal entry site (IRES)) targeting to silent or repressed genes in silenced loci, to separate genes with low-level expression at critical stage from the silent or repressed genes; (b) evaluating the efficiency of targeting to the silent or repressed genes; and (c) engineering a reporter system to facilitate targeting genes with low-level expression in the mammalian cell library to minimize the bias of targeting genes.

The advantages of the present invention comprise: (1) minimizing the bias of targeting genes located at "hot spots", the drawbacks seen in all of gene targeting technologies currently available; (2) advantageously targeting key genes involving in critical developmental decisions but are silenced or repressed in embryonic or other type of stem cells; and (3) avoiding the need of introducing antibiotic genes into the host genome and in turn eliminating potential threats of drifting antibiotic resistant genes into environment.

Hence, this invention provides an unprecedented genetic manipulation platform for efficiently altering genetic material at mammalian cell and organism levels without relying on the expression of targeted gene. Other objects and advantages of the present invention will carry out apparent from the specific embodiment disclosed in the following descriptions.

BRIEF DESCRIPTION OF THE DRAWINGS

The foregoing aspects and many of the attendant advantages of this invention will become more readily appreciated as the same becomes better understood by reference to the following detailed descriptions, when taken in conjunction with the accompanying drawings, wherein.

DETAILED DESCRIPTION OF THE INVENTION

Figure 1:
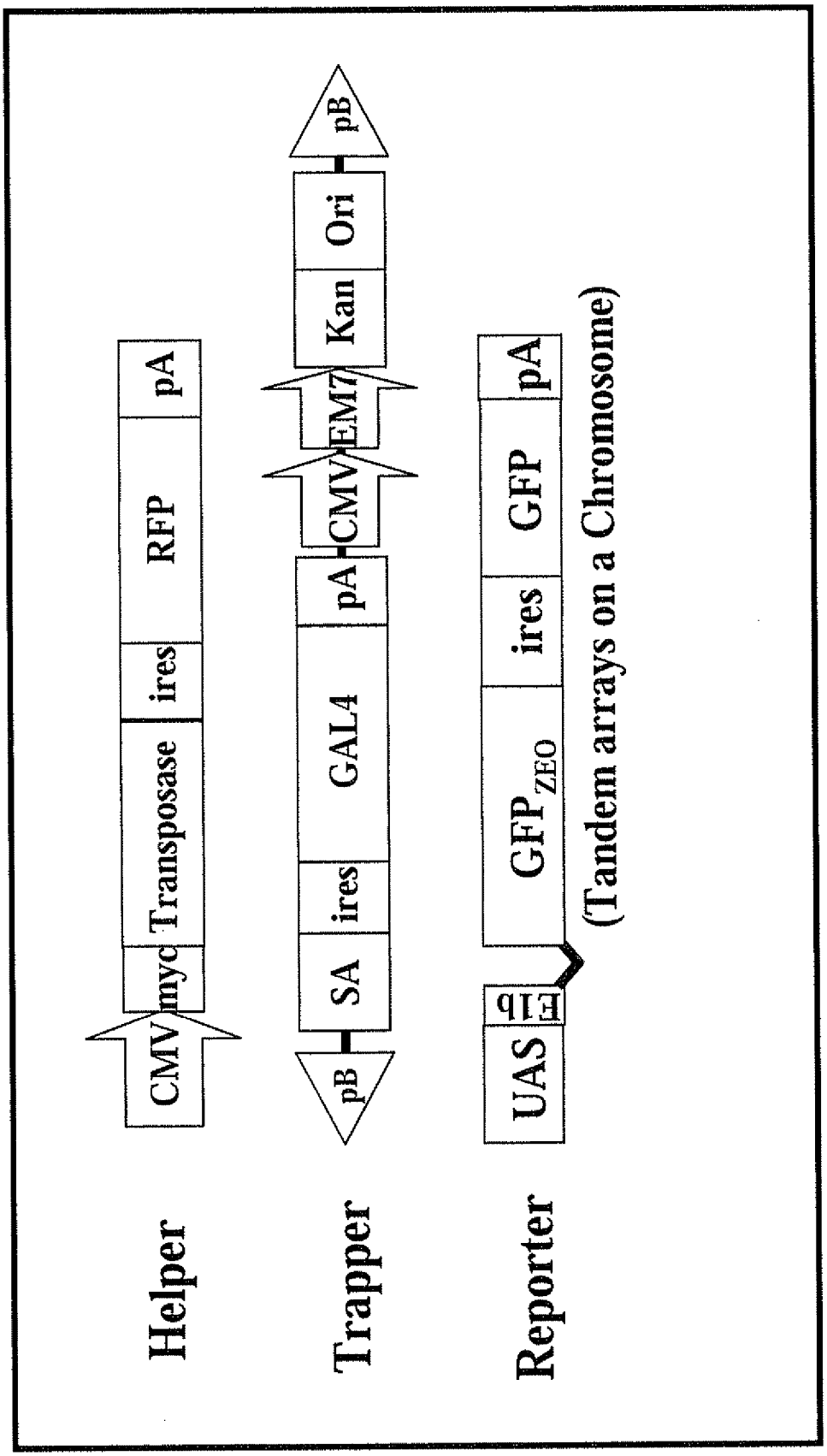
FIG. 1: The vectors in the piggyBac transposon used in the drug-free gene targeting system.

Reference will now be made in details to the embodiments of the present invention, examples of which are illustrated in the accompanying drawings. Wherever possible, the same reference numbers are used in the drawings and the description to refer to the same or like parts. Moreover, the components in the drawings are not necessarily to scale, emphasis instead of being placed upon clearly shown in the principles of the present invention.

Although in general the techniques mentioned herein are well known in the art, reference may be made in particular to Sambrook et al., Molecular Cloning, A Laboratory Manual (2001) 3rd edition, CSHL press, and Ausubel et al., Short Protocols in Molecular Biology (2003) 4th edition, John Wiley & Sons, Inc.

DESCRIPTION OF THE PREFERRED EMBODIMENT

The present invention provides a novel method and components thereof to provide a tool for efficient genetic modification, which are applied in the medical, pharmaceutical and livestock industries.

The method and components thereof are provided to waive the inevitable drug selection procedures during the process of genetic modification in cell lines or organisms. The genetic modification comprises at least one of gene manipulation, gene disruption, gene insertion, gene transgenesis and gene disrupted mammalian cell library establishments. In particularly, the process of the genetic modification is focused on targeting silent or repressed genes in cell lines or organisms. Furthermore, the cells adapted in targeting silent or repressed gene in gene disruption comprise stem cells including mammalian somatic, neuronal or embryonic stem cells.

The organism comprises a native or a genetic modified organism of multicellular eukaryotic organisms, which is intended an animal or a plant but not limited to the cell lines and more preferably is a mammal.

Simultaneously, the animal comprises one of selected from the phyla cnidaria, ctenophora, platyhelminthes, nematoda, annelida, mollusca, chelicerata, uniramia, crustacea and chordata. The uniramia comprises the subphylum hexapoda that includes insects such as the winged insects. The chordata comprises one or more of vertebrate groups such as mammals, birds, reptiles and amphibians. In particularly, the preferred embodiment of the mammals include non-human primates, cats, dogs or ungulates such as cows, goats, pigs, sheep, horses and rodents such as mice, rats, gerbils and hamsters.

In the case of the plant comprises at least one of the seed-bearing plants including angiosperms and conifers, wherein the angiosperms include dicotyledonous plants and monocotyledonous plants. The preferred examples of the dicotyledonous plants include a group of selected from tobacco (*Nicotiana plumbaginifolia* and *Nicotiana tabacum*), arabidopsis (*Arabidopsis thaliana*), *Brassica napus*, *Brassica nigra*, *Datura innoxia*, *Vicia narbonensis*, *Vicia faba*., pea (*Pisum sativum*), cauliflower, carnation and lentil (*Lens culinaris*). The preferred embodiments of the monocotyledonous plants comprise cereals such as wheat, barley, oats and maize.

1. The Method to Waive the Inevitable Drug Selection Procedures Selection

An embodiment of methods for performing the drug-free selection is preferably mediated by transposases, but not limited to the other enzymes for genetic modification. Moreover, the gene transgenic or disruption organisms comprises one or more insertions of the elements mediated by the piggyBac transposase that is preferable the piggyBac-like transposon, but not limited to other transposases, recombinases, or viral integrases.

The components and procedures being adapted to the piggyBac-like transposon in the present invention that addressed to achieve the drug-free selection for gene modification include: (a) trapper constructs and helper constructs; (b) a reporter system; and (c) the culture and selection procedures in the drug-free environments; (d) the evaluation procedures for the efficiency of silent genes targeting; and (e) the verification process of targeted genes.

The embodiment of the present invention further provides a method for drug-free selection performing genetic manipulation, which comprises the steps of (a) generating a trapped mammalian cell library, such as a trapped mouse stem cell library in the exemplary embodiment, enriched by the trapper constructs (including the element of piggyBac terminal inverted repeats (TIRs)) and the helper constructs (including a sequence of a internal ribosomal entry site (IRES)) targeting to silent or repressed genes in silenced loci, to separate genes with low-level expression at critical stage from the silent or repressed genes; (b) evaluating the efficiency of targeting to the silent or repressed genes; and (c) engineering the reporter system to facilitate targeting genes with low-level expression in the mammalian cell library to minimize the bias of targeting genes.

2. Components of the Trapper Construct

In a preferred embodiment, the trapper construct contains the element of terminal inverted repeats (TIRs). Referred to sequence listings of the trapper construct of the piggyBac tranaposon (total length 11504 bp of the trapper construct represented to the end of this specification), it preferably uses a total 122 bp including both left and right short TIRs, but not limited to the wildtype piggyBac TIRs.

FIG. 1 is represented to the vectors of the piggyBac transposon used in the drug-free gene targeting platform. Three major components in the piggyBac transposon include: (1) the helper construct; (2) the trapper construct; and (3) the reporter system, wherein the helper construct contains two independent transcripts (namely, the coding sequence of piggyBac transposase and red fluorescence protein (RFP as describes herein)) driven by the human cytomegalovirus (CMV) promoter.

In the FIG. 1, the trapper construct contains 122 nucleotides including the left and right terminal inverted repeats (TIRs) bracketing the splicing acceptor (SA), the internal ribosomal entry site(IRES), the coding sequence of the yeast GAL4 transcription factor, and a rescue cassette. Between the left and right terminal inverted repeats, it cargos the splicing acceptor (SA) sequence, three stop codons in different reading frames, a internal ribosomal entry site (IRES), the coding of yeast GAL4 transcription factor, a polyadenylation signal sequence, a bacteria chloramphenicol resistant gene, and a PUC replication region.

The rescue cassette contains a bacterial chloramphenicol resistant gene and the PUC replication origin to facilitate the retrieval of chromosomal sequence information franking the insertion site of the trapper construct. The reporter system contains two independent GFP transcripts under the control of yeast upstream activation sequence (UAS). The reporter system was inserted into the genome in a tandem array fashion. Thus, the reporter system will not have the positional effect as seen in the prior arts of which the trapper construct also carries the reporter construct. Therefore, the signal of the GFP reporter will be amplified through a cascaded transcriptional regulation. Therefore, the GFP signal can be detected even in clones with trapper inserted in genes with low expression level.

3. Components of the Helper Construct

As illustrated on the FIG. 1, the helper construct contains a sequence of IRES which links the coding of piggyBac transposase and red fluorescence protein (RFP). Both coding sequences are driven by human cytomegalovirus (CMV) promoter. At the end of RFP coding sequence, there is a polyadenylation signal sequence to maintain the stability of both transcripts. Additionally, the piggyBac transposase can be provided as DNA encoding as describe above or as the form of protein or RNA.

Further, promoters or other expression control regions can be linked with the nucleic acid encoding the piggyBac transposase to regulate the expression of the protein in a quantitative or in a tissue-specific manner.

4. Components of the Reporter System

In the case of the reporter system contains two copies of green fluorescent protein (GFP) coding sequence and is under the control of yeast upstream activation sequence (UAS) sequence and an E1b minimal promoter. As shown in FIG. 1, in order to facilitate the GFP expression, there is an intron sequence between the E1b promoter and the start codon of GFP.

In a preferred embodiment, a C17.2 cell line that is an immortalized mouse neural stem cell (Snyder, et al., 1992) was used to build the reporter system. As depicted on the FIG. 2, it illustrates the engineered C17.2 cell harboring the tandem array of GFP reporter, wherein the photograph (A) represents to the C17.2 cell lines carried the tandem array of GFP. Without the expression of the GAL4 transcription factor, no background GFP signal is detected. The photograph (B) represents to the GFP signal can be detected under a fluorescence microscopy after introducing the trapper construct and the helper construct into this engineered cell line C17.2. In any case, the various GFP intensity detected in each individual clone likely represents the various strength of promoter activity of different trapped genes.

In addition to the established cell line, the reporter system can be built in different stem cells and primary cell cultures if primary cells can duplicate in the in vitro cell culture system for a certain period of time; for example, the human umbilical stem cell (Lu, et al., 2005; Fu, et al., 2006). On the other side, the reporter construct gene sequences in the present invention can be an enzyme (e.g. beta-lactamase, beta-galactosidase, luciferase, chloramphenicol acetyltransferase), bioluminescent, chemiluminescent or fluorescent molecule. In the preferred embodiments, the marker is green fluorescent protein (GFP) or a mutant thereof, such as a mutant GFP having an altered fluorescence wavelength, increased fluorescence, or both. In the best mode of the embodiments, the mutant GFP is intended blue GFP and the fluorescent molecule is also adapted to red fluorescent protein or yellow fluorescent protein.

As the GFP is an embodiment reporter system directly controlled by the expression of yeast GAL4 transcription factor which is regulated by the targeted gene's promoter, the reporter signal will be amplified by this cascaded transcription regulations, and therefore can detect a subtle gene expression by bringing up the reporter signal to a visually detectable level.

Figure 2:
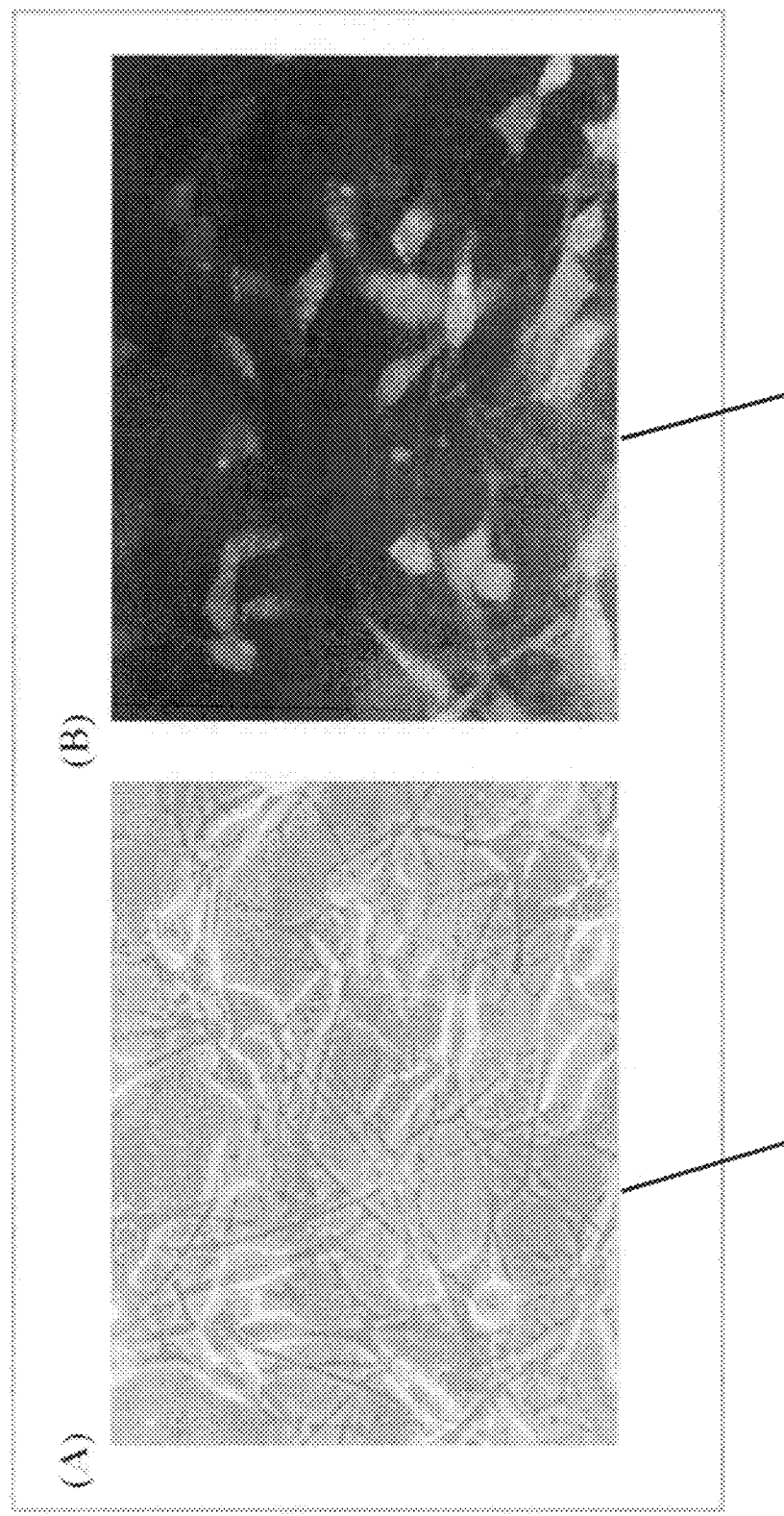
FIG. 2(A) and FIG. 2(B): The engineered C17.2 cell harbored the tandem array of a GFP reporter system.

The reporter system was linealized by the NotI restriction enzyme to facilitate the DNA chromosomal integration without disrupting the coding of GFP reporter. The linealized reporter was transfected into the C17.2 cells and zerocin was used to select the recombinant clones 24 hours post transfection. Several zerocin resistant clones were selected and examined under the fluorescence microscope. As the FIG. 2 shown, few GFP negative clones were isolated to ensure the zero fluorescence background. Further, to test this built-in reporter system in the selected clones, the GAL4 transcription factor was introduced into those clones to simulate the trapping situation and to observe the intensity of GFP signal in each clone. Several GAL4 responsive clones were identified to serve as the reporter lines.

The advantages of the present invention comprise: (1) minimizing the bias of targeting genes located at "hot spots", the drawbacks seen in all of gene targeting technologies currently available; (2) advantageously targeting key genes involving in critical developmental decisions but are silenced or repressed in embryonic or other type of stem cells; and (3) avoiding the need of introducing antibiotic genes into the host genome and in turn eliminating potential threats of drifting antibiotic resistant genes into environment.

Hence, this invention provides an unprecedented genetic manipulation platform for efficiently altering genetic material at mammalian cell and organism levels without relying on the target gene expression.

5. Procedures of Performing Drug-free Selection for Genetic Modifications

The present invention also provides procedures of performing drug-free selection for genetic modification, which comprises the steps of (a) generating a trapped mouse stem cell library enriched by targeting to the silenced loci; (b) evaluating the efficiency of targeting to silent or repressed genes; (c) engineering a dual reporter system to facilitate targeting genes with low level of gene expression.

Furthermore, the present invention is disclosed a method for drug-free selection of performing genetic modification, which comprises the steps of (a) generating a trapped mammalian cell library by the trapper constructs (including the element of piggyBac terminal inverted repeats (TIRs)) and the helper constructs (including a sequence of a internal ribosomal entry site (IRES)) targeting to silent or repressed genes in silenced loci, to separate genes with low-level expression at critical stage from the silent or repressed genes; (b) evaluating the efficiency of targeting to the silent or repressed genes; and (c) engineering the reporter system to facilitate targeting genes with low-level expression in the mammalian cell library to minimize the bias of targeting genes.

5.1. Delivering Trapper and Helper Constructs into Cells

The piggyBac transposon in the present invention can be introduced into one or more cells using any of a variety of techniques known in the art such as, but not limited to microinjection, lipofectin, particle bombardment, electroporation, DNA condensing reagents (e.g., calcium phosphate, polylysine or polyethyleneimine) or incorporating the transposons into an adenoviral vector and infecting the virally packaged transposon vector with the cell.

Figure 3:
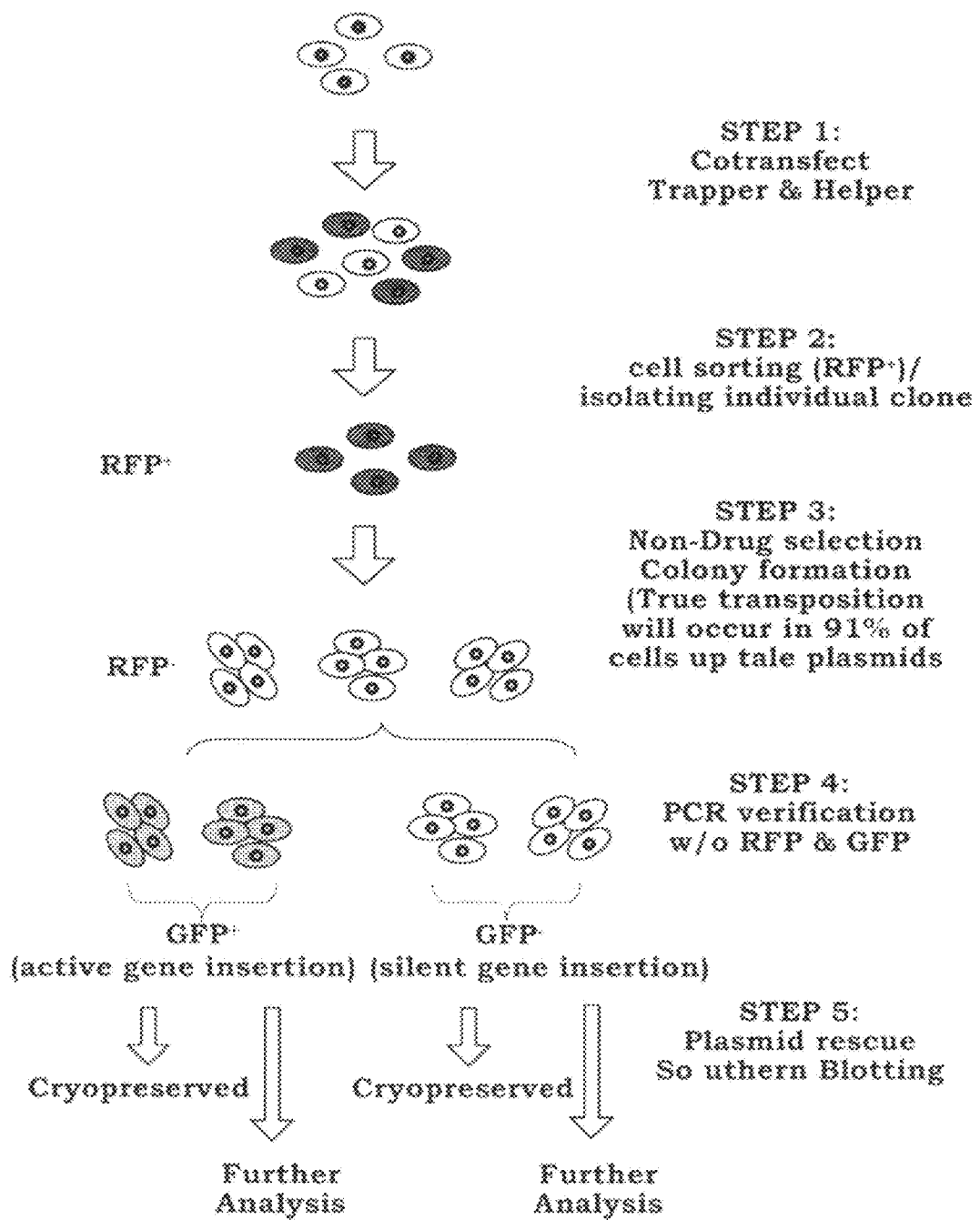
FIG. 3: The drug-free selection scheme by the piggyBac gene targeting system.

FIG. 3 is depicted the drug-free selection scheme by the piggyBac gene targeting system. Both the trapper construct and the helper construct will be delivered into cells with the molar ratio of 1:1 (step1). Since the helper construct contains reporter gene (RFP), cells receiving the plasmid will be RFP positive. After post-transfection, cells are subjected to a cell sorter to isolate the RFP positive cells (step2). The individual RFP cells isolated will be cultured and cloned under non-drug selection environment (step3). After culturing, some clones will display GFP signal and the others are GFP negative. Since the piggyBac-mediated chromosomal insertion rate is more than 91%, clones with and without GFP signal likely represent cells with piggyBac targeting to the active expression genes and to the silent or repressed genes or chromosomal regions, respectively. The individual clone will be duplicated and divided into two parts; one part is subject to cryo-preservation (step4), and the other will be further analyzed to identify its target site in the genome (step5).

5.2. Cell Sorting

Figure 4:
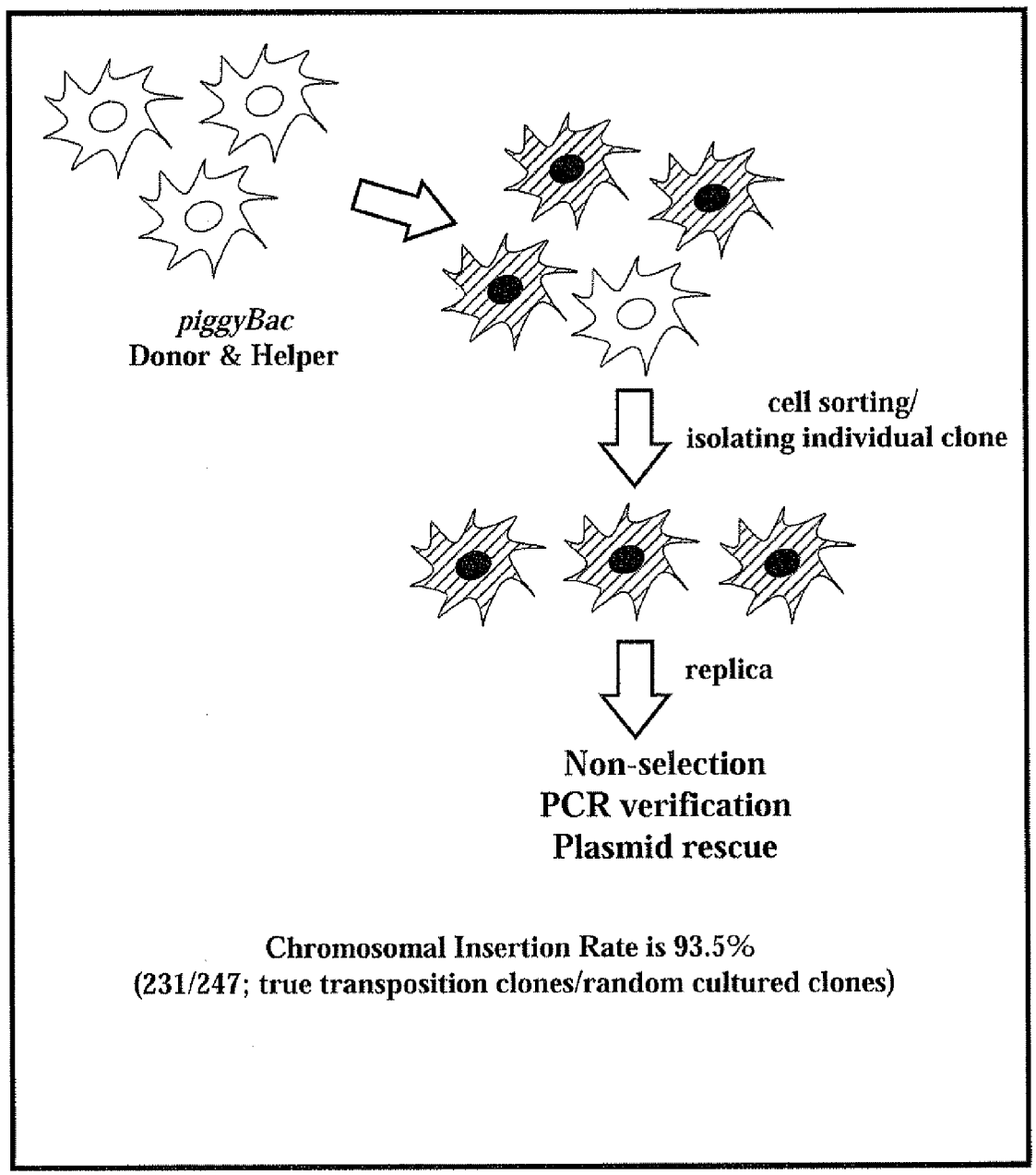
FIG. 4: piggyBac Chromosome Insertion Rate.

FIG. 4 is a scheme of the piggyBac Chromosome Insertion Rate that addresses the result of the piggyBac-mediated chromosome insertion rate without being interfered by the efficiency of the DNA transfection. The experiments were performed in human HEK293 cells. First of all, the cells were transfected with both trapper and helper constructs by FuGene (Roche-applied Science). The donor plasmid contains terminal inverted repeats of piggyBac bracketing hygromycin expression cassette and the plasmid rescue cassette.

The helper construct contains the piggyBac transposase and GFP coding sequences separated by IRES. Both transcripts were under the control of CMV promoter. After transfecting both donor and helper plasmids with 1:1 molar ratio, the cells harboring both plasmids will display a GFP positive signal. To isolate the GFP positive population, the transfected cells were subjected to a cell sorter. Since the GFP positive cells represent the cells harboring at least the helper plasmids, the efficiency of DNA transfection unlikely has influence on determining chromosomal insertion rate.

Individual cells were grown in non-drug selection medium to allow colony formation. 247 individual clones were then randomly isolated and determined for the occurrence of the piggyBac-mediated transposition event. 231 out of these 247 randomly selected clones were verified to bear piggyBac inserts with the canonical TTAA-targeted sequence. The result suggests that the piggyBac-mediated transposition rate reaches up to 93.5% (231/247) in cells carrying at least the helper construct.

As illustrated on the FIG. 4, one to one molar ratios of donor and the helper construct should be employed into cells. Southern blots probing with a specific nucleotide sequence can be performed in individual clone to verify the copy number of insertion. The cells harboring at least the helper construct can be harvested by a fluorescence activated cell sorter (FACS). Since our helper plasmid contains the coding region of RFP and the transposase in a bi-cistronic transcription unit regulated by the CMV promoter, the RFP positive cell population is likely to have the functional transposase with the trapper construct as well. Following such procedures, a true transposition event should occur in 93.5% of RFP positive cells.

5.3. Colony Formation with Drug-Free Selection

After sorting cells with the fluorescence activated cell sorter (FACS), the RFP positive cells should be cultured in a low density to facilitate the isolation of individual clones. For the purpose of unbiased gene targeting that ensures the equal chance of targeting genes in both active and silence chromosomal regions, the sorted cells should be cultured under the drug-free environment for colony formation.

Consequently the piggyBac transposon is able to target the silent regions in host chromosomes. As depicted on the FIG. 3 and FIG. 5, this scheme addresses the capability of piggyBac-mediating targeting in the silent regions of host chromosome. Both donor and the helper construct were cotransfected into HEK293 cells and the GFP positive population in transfected cells were isolated by a cell sorter.

Figure 5:
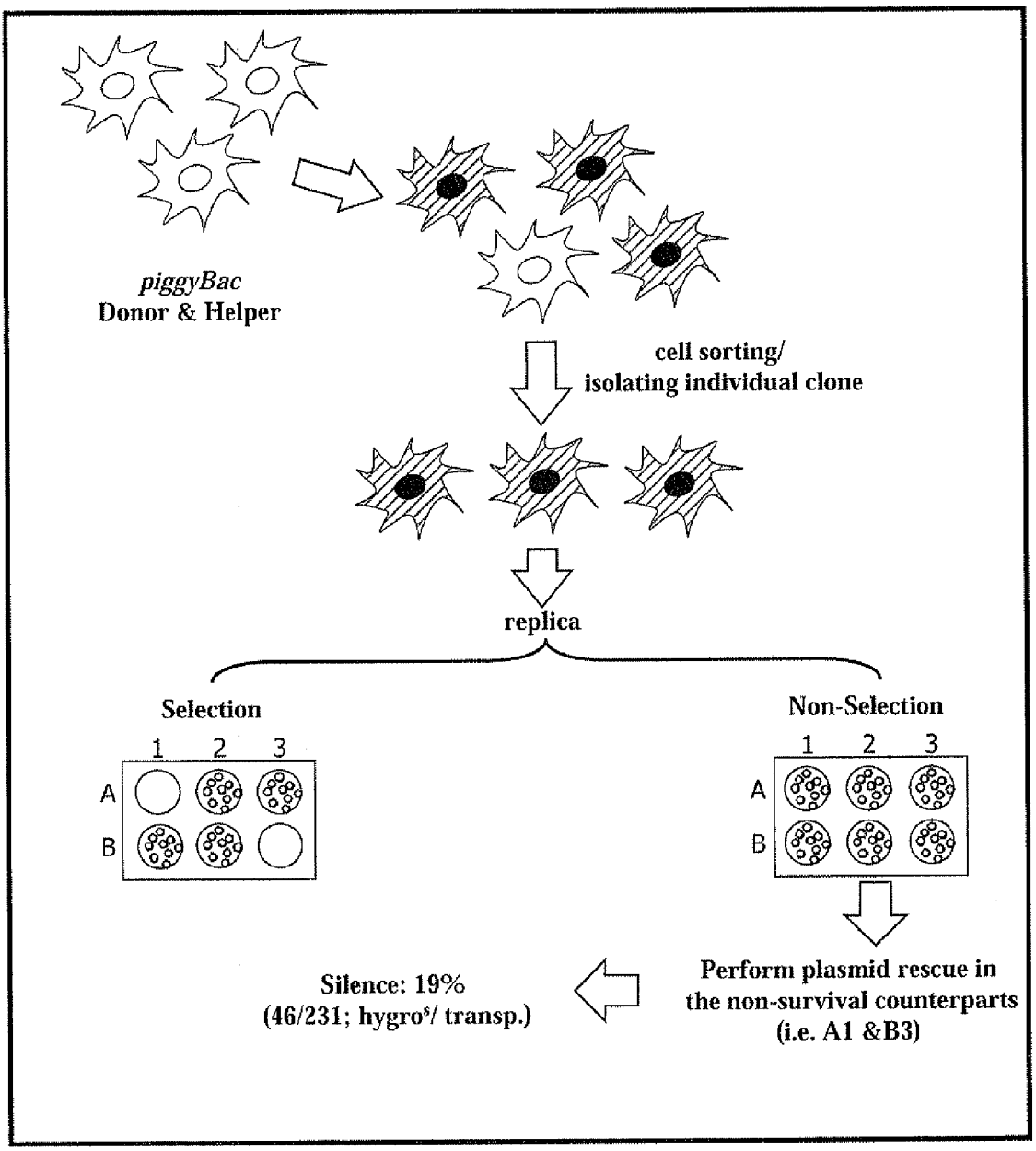
FIG. 5: piggyBac is able to access the silent regions in the targeted chromosomes.

After expanding individual clones, cells from each clone were divided into two parts as the FIG. 5 shown. One part of cells is cultured in the presence of hygromycin while the other part is grown in medium with drug-free selection. The clones which are sensitive to the drug (e.g. A1 & B3) were further verified for the existence of true transposition by performing plasmid rescue experiments using genomic DNA isolated from their drug-free selection counterparts. In the preferred mode of the embodiment, 8 out of 42 piggyBac clones with the true piggyBac-mediated transposition are sensitive to hygromycin selection, suggesting that piggyBac transposon is able to target silent region, and the target rate on silent chromosomal region is 19% (8/42) in human HEK293 cells.

As the step3 shown in the FIG. 3, two kinds of population in the cultured clones can be expected: (1) the GFP positive colonies represents cells with the trapper inserted in the actively expressing loci; (2) the GFP negative colonies represents cells with no inserts or with insets has located on the silent region of the chromosome.

Given the experimental result provided in FIG. 4, true transposition occurs in 93.5% of the cells carried at least the helper construct, the chance of obtaining clones without inserts is so small that it is worth the effort to isolate every single clones. Therefore, both GFP positive and negative clones should be isolated, expanded, and cryopreserved for later analysis.

The detailed procedure of handling GFP negative clones are as follows. In the FIG. 5, individual GFP negative clones can be identified under the inverted fluorescence microscope, and subsequently cloned by the use of the cloning ring. Once circling the desired clones with the cloning ring, 20 ul of 0.25% trypsin will be added to harvest the clones. The trypsinized cells can be transferred and cultured in the individual well of a 96-well plate. After the cells growing into confluency, individual clones should be expended to generate three copies for each 96-well plate and crypreserved. To further analyzing for its trapping efficiency in the silent chromosomal region, one copy of 96-well plates is thawed and the individually clones can be further expanded gradually until it reaches confluency in a 100 mm plate.

5.4. The Verification Process for the Efficiency of Silent Gene Targeting

Figure 6:
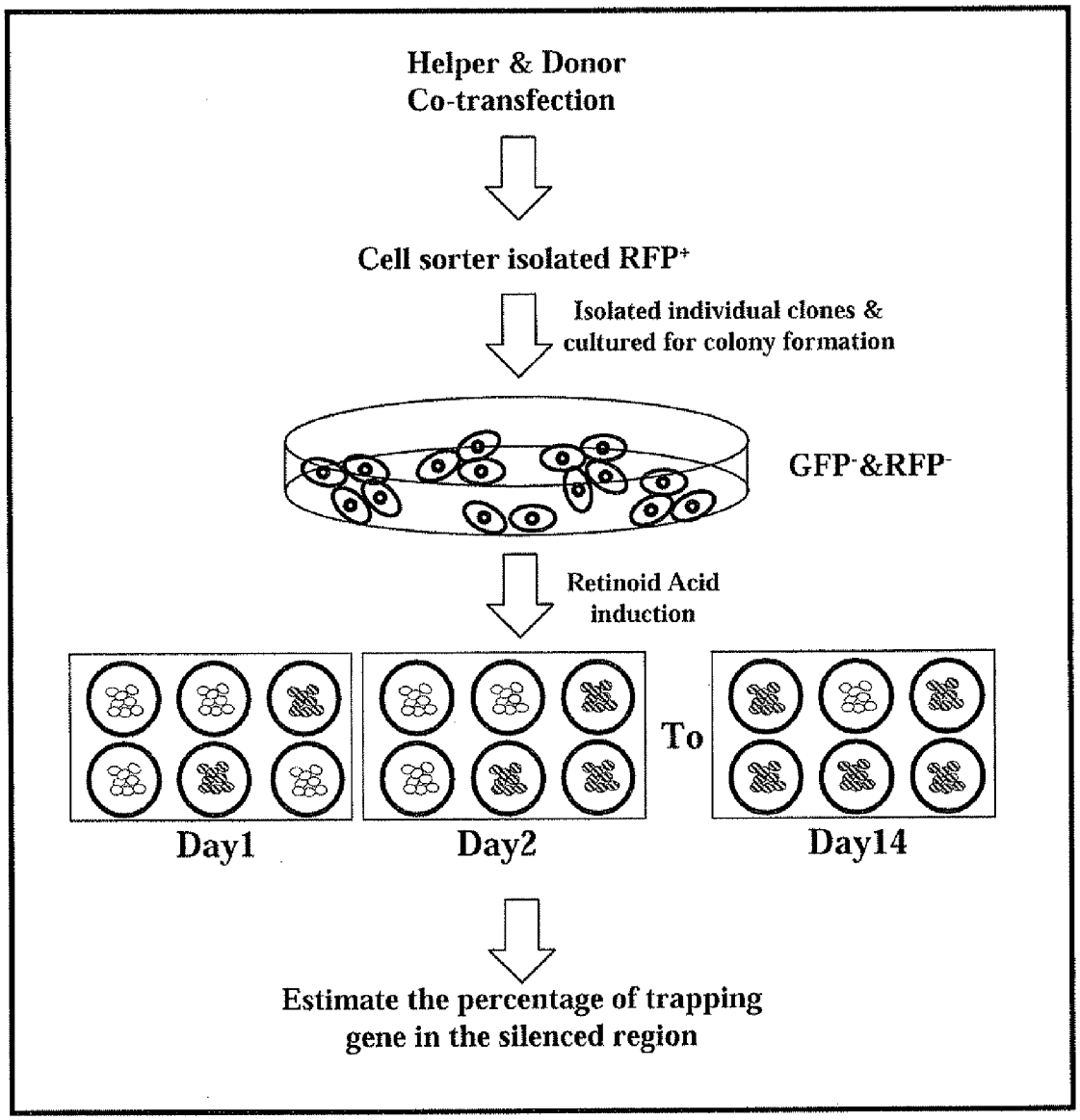
FIG. 6: The strategy for evaluation of gene trapping efficiency in the silent regions.

In the embodiment of the present invention, genes that are silenced in the C17.2 cell (an immortal mouse neural stem cell) but will be activated as the cells undergo neural differentiation after retinoid acid (RA) induction were applied to evaluate the efficiency of silent gene targeting in the present invention. To be continued with the FIG. 3, FIG. 6 are shown as a strategy for evaluation of gene trapping efficiency in the silent regions. Since the neurogenesis pathway is repressed in the undifferentiated stem cell, the profile of neural genes targeting will be served as an indicator for estimating the efficiency of silent or repressed genes trapping under the condition of non-drug selection.

The GFP negative clones (shown as the step5 in FIG. 3) represent the insertion occurred in the silent regions of the targeted genome. After cryopreservation, a copy of each individual clone will be propagated and further divided into two parts; one part of cells will be grown in regular stem cell medium, while the other part will be cultured in medium with Retinoid acid (RA) for the induction of neural differentiation.

Once cells are committed into a neuronal cell lineage, the expression of the GAL4 transcription factor will be turned on in those cells with the trapper inserted in genes involving in the neuronal cell lineage. Consequently, the GFP expression, controlled by GAL4 transcription factor will be detected according to the timing of the neural gene expression along the course of neural differentiation. A 14-day time course of RA induction will be applied to evaluate the efficiency of neural genes trapped in stem cells.

To maintain the pluripotency of the stem cells, the genes in those highly differentiated cell lineages like neural cell lineages should be absolutely silenced or repressed. Thus, the profile of the neurogenesis genes targeting is applicable to evaluate the efficiency of targeting aforementioned silent genes under the drug-free environments.

The individual GFP negative clones should be cultured in 6-well plates with the retinoid acid for the induction of neural differentiation. If the insertions locate on the neural genes silenced in the undifferentiated C17.2 cells, the progression of the neural differentiation will activate the expression of these genes and in turned switch on the GFP expression. In a two-week time course of RA induction, the number of emerging GFP clones from those originally identified as GFP negative in the un-differentiated states clones can be obtained. Thus, the efficiency of our drug-free approach can be evaluated.

To reveal the identity of genes that are targeted by the trapper construct and are expressed only as cells undergoing RA-induced neuronal differentiation, genomic DNA isolated from the undifferentiated counterpart of these clones can be subjected to the plasmid rescuing experiments to retrieve the chromosomal sequence information flanking their target site. In an exemplary embodiment, the genomic DNA can be extracted from cells by a genomic DNA extraction kit and digested by the SpeI restriction enzyme. After ligation by T4 DNA ligases, the DNAs should be transformed into bacterial competent cells to obtain plasmids carrying chromosomal DNA flanking the target site. The rescued plasmids can be purified by a plasmid purification kit and subjected to DNA sequencing.

Figure 7:
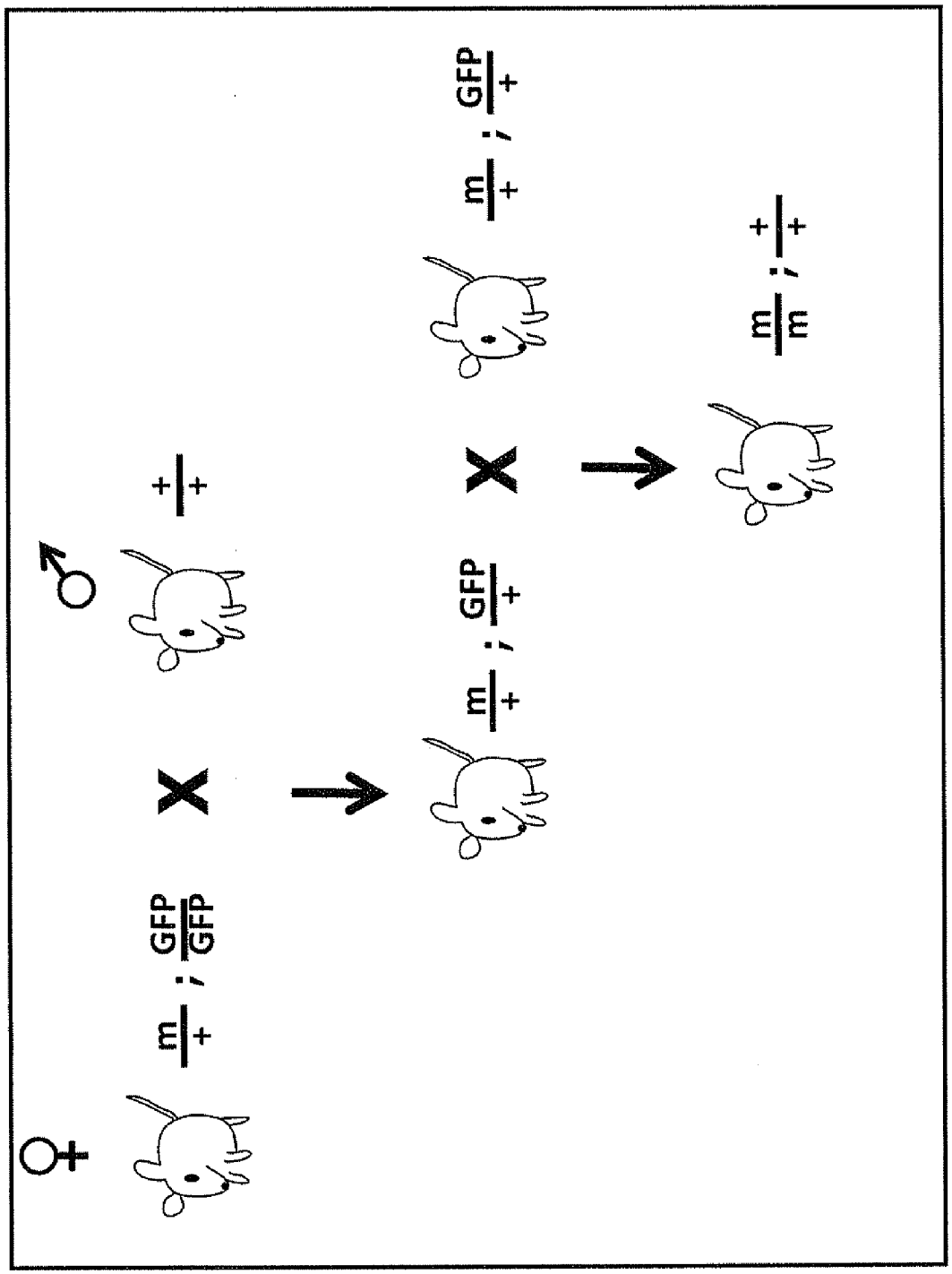
FIG. 7: Crossing out the GFP reporter system.

To avoid the potential effects on the phenotypic analysis, the reporter system can be removed by crossing with a wild type animal. Thus, while restoring the wild type genome background and eliminating the unawareness of background mutations, the animal can still keep the targeted gene disrupted. As depicted on FIG. 7, the reporter system in a trapped mouse can be removed by crossing the mouse with the wild type mouse. To eliminate the potential background mutation as well as the interference derived from gfp reporter system, the knock out mouse can be bred with wild type mice to obtain a gene disruption mouse without bearing the reporter system.

Based on the above, the present invention provides the method and components thereof of performing genetic modifications mediated by the piggyBac-like transposon under drug-free selection environment. In accordance with the following findings: (1) the chromosomal insertion rate of piggyBac-like transposon reaches 93.5%; (2) the piggyBac-like transposon is able to target to the silent regions on human chromosomes. These evidences are strongly support the feasibility of performing genetic alternation without requirement of drug-selection under specific identified conditions. This novel invention counteracts the traditional drug selection-dependent strategies that greatly bias the gene targeting toward actively expressing genes or active chromosomal regions. Further, given that the drug selection requires the incorporation of antibiotic resistant genes into the genome of transgenic organisms, such genome modification in the transgenic animals may cause biohazards as those genes drifted into natural environments. Therefore, the present invention creates an unprecedented strategy leading to an unbiased gene targeting repertoire in genome manipulation or disruption as well as minimizing the potential biohazards which the transgenic organisms may cause to environment.

The foregoing detailed description is for the purpose of illustration. It will be apparent to those skilled in the art that various modifications and variations can be made to the structure of the present invention without departing from the scope or spirit of the invention. In view of the foregoing, it is intended that the present invention cover modifications and variations of this invention provided they fall within the spirit and scope of the following claims and their equivalents.

6. Sequence Listings of Various Components of the Piggybac Transposon 6.1. Trapper Construct (total length of 11504 bp) (SEQ ID NO: 1)

```
gacggatcgggagatctcccgatcccctatggtgcactctcagtacaa
tctgctctgatgccgcatagttaagccagtatctgctccctgcttgtg
tgttggaggtcgctgagtagtcgcgagcaaaatttaagctacaacaa
ggcaaggcttgaccgacaattgcatgaagaatctgcttagggttaggc
gttttgcgctgcttcgcgatgtacgggccagatatacgcgttgacatt
gattattgactagttattaatagtaatcaattacggggtcattagttc
atagcccatatatggagttccgcgttacataacttacggtaaatggcc
cgcctggctgaccgcccaacgaccccgcccattgacgtcaataatga
cgtatgttcccatagtaacgccaatagggactttccattgacgtcaat
gggtggagtatttacggtaaactgcccacttggcagtacatcaagtgt
atcatatgccaagtacgccccctattgacgtcaatgacggtaaatggc
ccgcctggcattatgcccagtacatgacttatgggactttcctactt
ggcagtacatctacgtattagtcatcgctattaccatggcaattcatg
ggaagaggaaccgaaagtatgttttcagatgttctttctcagaaata
ggagtttgcggaggttggagtgtgtgttgtaggacacgaacccagg
tggaggagactggaggacagagccctctttcccagggagggaaggagg
agagtttgagatccgctccggaagtcggggttcaggtttgagcaggcc
aggcctctcccgtggtctcgccctcttgtcctagaagcctcactggcc
aggtgtaagccaggtcgtgggtgccgagccctgctccctcatcctcag
catggatgtgaagaggactgtatggcgtgcgggtgtgtgtgaccgtgg
gtacacttaaaacaccgggttttggatctgcactgtcccggatgtcct
ctggtgctcaaagacccttttgggtttgccctttggtaagagcgccgg
gatctacttgtctggaggccagggagtcctcagccgaggcttgccgcc
cctgactgcactgcactgagtagtggatgggagagtctggtaccgcac
tgccggtttcctccaccatccccgcagcgcagggcagtgcattccgtc
ctggctgcgaaggggggatggtcgggccttctccagcctcttccgcttc
tagcgaaggggccttgatggaagggcccgcatgtctccaaagttgatt
catgcttcttgcacagagaaagaccagaaagaaggtctcaagttttag
ccggtagcccggatggccttttcctgcacggcaccatatgaaccttgt
gaccctgactttgagacccctctaacccaaggcccctaccactttacc
cttttcctttgaaggctttcccacaccaccctccacacttccccaaac
actgccaactatgtaggaggaagggttgggactaacagaagaacccg
ttgtggggaagctgttgggagggtcactttatgttcttgcccaaggtc
agttgggtggcctgcttctgatgaggtggtcccaaggtctgggtaga
aggtgagagggacaggccaccaaggtcagcccccccccctatcccat
aggagccaggtccctctcctggacaggaagactgaagggagatgcca
gagactcagtgaagcctggggtaccctattggagtccttcaaggaaac
aaacttggcctcaccaggcctcagccttggctcctcctgggaactcta
ctgcccttgggatcccttgtagttgtgggttacataggaagggacgg
attcccctttgactggctagcctactcttttcttcagtcttctccatct
cctctcaccgttctctcgacccttttccctaggatagacttggaaaaag
ataaggggagaaaaacaaatgcaaacgaggccagaaagattttggctg
ggcattccttccgctagcttttattgggatcccctagtttgtgatagg
```

-continued

```
ccttttagctacatctgccaatccatctcattttcacacacacaca
ccactttccttctggtcagtgggcacatgtccagcctcaagtttatat
caccaccccaatgcccaacacttgtatggccttggcgggtcatccc
cccccaccccagtatctgcaacctcaagctagcttgggtgcgttgg
ttgtggataagtagctagactccagcaaccagtaacctctgcccttc
tcctcCATGACAACCAGgtcccaggtcccgaaaaccTGAgTAGgTAAa
gatctcaattggggcccctatagtgtcacctaaataattccgcccccc
cctctccctccccccccctaacgttactggccgaagccgcttggaat
aaggccggtgtgcgtttgtctatatgttattttccaccatattgccgt
cttttggcaatgtgagggcccggaaacctggccctgtcttcttgacga
gcattcctaggggtctttcccctctcgccaaaggaatgcaaggtctgt
tgaatgtcgtgaaggaagcagttcctctggaagcttcttgaagacaaa
caacgtctgtagcgacccttttgcaggcagcggaacccccacctggcg
acaggtgcctctgcggccaaaagccacgtgtataagatacacctgcaa
aggcggcacaacccagtgccacgttgtgagtggatagttgtggaaa
gagtcaaatggctctcctcaagcgtattcaacaagggctgaaggatg
cccagaaggtacccccattgtatgggatctgatctggggcctcggtgca
catgctttacatgtgtttagtcgaggttaaaaaaacgtctaggccccc
cgaaccacgggacgtggttttcctttgaaaaacacgatgataatATG
gaattcaccATGACCCCCCCCAAGAAGAAGCGCAAGGTGGAGGACGGA
ATGAAGCTACTGTCTTCTATCGAACAAGCATGCGATATTTGCCGACTT
AAAAAGCTCAAGTGCTCCAAAGAAAAACCGAAGTGCGCCAAGTGTCTG
AAGAACAACTGGGAGTGTCGCTACTCTCCCAAAACCAAAAGGTCTCCG
CTGACTAGGGCACATCTGACAGAAGTGGAATCAAGGCTAGAAAGACTG
GAACAGCTATTTCTACTGATTTTTCCTCGAGAAGACCTTGACATGATT
TTGAAAATGGATTCTTTACAGGATATAAAAGCATTGTTAACAGGATTA
TTTGTACAAGATAATGTGAATAAAGATGCCGTCACAGATAGATTGGCT
TCAGTGGAGACTGATATGCCTCTAACATTGAGACAGCATAGAATAAGT
GCGACATCATCATCGGAAGAGAGTAGTAACAAAGGTCAAAGACAGTTG
ACTGTATCGATTGACTCGGCAGCTCATCATGATAACTCCACAATTCCG
TTGGATTTTATGCCCAGGGATGCTCTTCATGGATTTGATTGGTCTGAA
GAGGATGACATGTCGGATGGCTTGCCCTTCCTGAAAACGGACCCCAAC
AATAATGGGTTCTTTGGCGACGGTTCTCTCTTATGTATTCTTCGATCT
ATTGGCTTTAAACCGGAAAATTACACGAACTCTAACGTTAACAGGCTC
CCGACCATGATTACGGATAGATACACGTTGGCTTCTAGATCCACAACA
TCCCGTTTACTTCAAAGTTATCTCAATAATTTTCACCCCTACTGCCCT
ATCGTGCACTCACCGACGCTAATGATGTTGTATAATAACCAGATTGAA
ATCGCGTCGAAGGATCAATGGCAAATCCTTTTTAACTGCATATTAGCC
ATTGGAGCCTGGTGTATAGAGGGGGAATCTACTGATATAGATGTTTTT
TACTATCAAAATGCTAAATCTCATTTGACGAGCAAGGTCTTCGAGTCA
GGTTCCATAATTTTGGTGACAGCCCTACATCTTCTGTCGCGATATACA
```

-continued

```
CAGTGGAGGCAGAAAACAAATACTAGCTATAATTTTCACAGCTTTTCC
ATAAGAATGGCCATATCATTGGGCTTGAATAGGGACCTCCCCTCGTCC
TTCAGTGATAGCAGCATTCTGGAACAAAGACGCCGAATTTGGTGGTCT
GTCTACTCTTGGGAGATCCAATTGTCCCTGCTTTATGGTCGATCCATC
CAGCTTTCTCAGAATACAATCTCCTTCCCTTCTTCTGTCGACGATGTG
CAGCGTACCACAACAGGTCCCACCATATATCATGGCATCATTGAAACA
GCAAGGCTCTTACAAGTTTTCACAAAAATCTATGAACTAGACAAAACA
GTAACTGCAGAAAAAGTCCTATATGTGCAAAAAAATGCTTGATGATT
TGTAATGAGATTGAGGAGGTTTCGAGACAGGCACCAAAGTTTTTACAA
ATGGATATTTCCACCACCGCTCTAACCAATTTGTTGAAGGAACACCCT
TGGCTATCCTTTACAAGATTCGAACTGAAGTGGAAACAGTTGTCTCTT
ATCATTTATGTATTAAGAGATTTTTTCACTAATTTTACCCAGAAAAAG
TCACAACTAGAACAGGATCAAATGATCATCAAAGTTATGAAGTTAAA
CGATGCTCCATCATGTTAAGCGATGCAGCACAAAGAACTGTTATGTCT
GTAAGTAGCTATATGGACAATCATAATGTCACCCCATATTTTGCCTGG
AATTGTTCTTATTACTTGTTCAATGCAGTCCTAGTACCCATAAAGACT
CTACTCTCAAACTCAAAATCGAATGCTGAGAATAACGAGACCGCACAA
TTATTACAACAAATTAACACTGTTCTGATGCTATTAAAAAACTGGCC
ACTTTTAAAATCCAGACTTGTGAAAAATACATTCAAGTACTGGAAGAG
GTATGTGCGCCGTTTCTGTTATCACAGTGTGCAATCCCATTACCGCAT
ATCAGTTATAACAATAGTAATGGTAGCGCCATTAAAAATATTGTCGGT
TCTGCAACTATCGCCCAATACCCTACTCTTCCGGAGGAAAATGTCAAC
AATATCAGTGTTAAATATGTTTCTCCTGGCTCAGTAGGGCCTTCACCT
GTGCCATTGAAATCAGGAGCAAGTTTCAGTGATCTAGTCAAGCTGTTA
TCTAACCGTCCACCCTCTCGTAACTCTCCAGTGACAATACCAAGAAGC
ACACCTTCGCATCGCTCAGTCACGCCTTTTCTAGGGCAACAGCAACAG
CTGCAATCATTAGTGCCACTGACCCCGTCTGCTTTGTTTGGTGGCGCC
AATTTTAATCAAAGTGGGAATATTGCTGATAGCTCATTGTCCTTCACT
TTCACTAACAGTAGCAACGGTCCGAACCTCATAACAACTCAAACAAAT
TCTCAAGCGCTTTCACAACCAATTGCCTCCTCTAACGTTCATGATAAC
TTCATGAATAATGAAATCACGGCTAGTAAAATTGATGATGGTAATAAT
TCAAAACCACTGTCACCTGGTTGGACGGACCAAACTGCGTATAACGCG
TTTGGAATCACTACAGGGATGTTAATACCACTACAATGGATGATGTA
TATAACTATCTATTCGATGATGAAGATACCCCACCAAACCCAAAAAAA
GAGTAAatgaatcgtagatactgaaaaaccccgcaagttcacttcaa
ctgtgcatcgtgcaccatctcaatttctttcatttatacatcgttttg
ccttcttttatgtaactatactcctctaagtttcaatcttggccatgt
aacctctgatctatagaatttttttaaatgactagaattaatgcccatc
ttttttttggacctaaattcttcatgaaaatatattacgagggcttat
tcagaagcttatcgataccgtcgacctcgagggggggcccgtttaaac
```

-continued ccgctgatcagcctcgactgtgccttctagttgccagccatctgttgt
ttgcccctccccgtgccttccttgacccctggaaggtgccactcccac
tgtcctttcctaataaaatgaggaaattgcatcgcattgtctgagtag
gtgtcattctattctgggggtgggtggggcaggacagcaaggggga
ggattgggaagacaatagcaggcatgctggggatgcggtgggctctat
ggcttctgaggcggaaagaaccagctgggctctaggggtatcccca
cgcgccctgtagcggcgcattaagcgcggcgggtgtggtggttacgcg
cagcgtgaccgctacacttgccagcgccctagcgcccgctccttttcgc
tttcttcccttcctttctcgccacgttcgccggtgtccgttacataac
ttacggtaaatggcccgcctggctgaccgccaacgaccccgcccat
tgacgtcaataatgacgtatgttcccatagtaacgccaatagggactt
tccattgacgtcaatgggtggagtatttacggtaaactgcccacttgg
cagtacatcaagtgtatcatatgccaagtacgccccctattgacgtca
atgacggtaaatggcccgcctggcattatgcccagtacatgaccttat
gggactttcctacttggcagtacatctacgtattagtcatcgctatta
ccatggtgatgcggttttggcagtacatcaatgggcgtggatagcggt
ttgactcacggggatttccaagtctccaccccattgacgtcaatggga
gtttgttttggcaccaaaatcaacgggactttccaaaatgtcgtaaca
actccgccccattgacgcaaatgggcggtaggcgtgtacggtgggagg
tctatataagcagagctcgtttagtgaaccgtcagatcgcctggagac
gccatccacgctgttttgacctccatagaagacaccgggaccgatcca
gcctccgcggactagtccgggaacggtgcattggaacggaccgtgttg
acaattaatcatcggcatagtatatcggcatagtataatacgacaagg
tgaggaactaaaccatggctagcATGATTGAACAAGATGGATTGCACG
CAGGTTCTCCGGCCGCTTGGGTGGAGAGGCTATTCGGCTATGACTGGG
CACAACAGACAATCGGCTGCTCTGATGCCGCCGTGTTCCGGCTGTCAG
CGCAGGGGCGCCCGGTTCTTTTTGTCAAGACCGACCTGTCCGGTGCCC
TGAATGAACTGCAAGACGAGGCAGCGCGGCTATCGTGGCTGGCCACGA
CGGGCGTTCCTTGCGCAGCTGTGCTCGACGTTGTCACTGAAGCGGGAA
GGGACTGGCTGCTATTGGGCGAAGTGCCGGGGCAGGATCTCCTGTCAT
CTCACCTTGCTCCTGCCGAGAAAGTATCCATCATGGCTGATGCAATGC
GGCGGCTGCATACGCTTGATCCGGCTACCTGCCCATTCGACCACCAAG
CGAAACATCGCATCGAGCGAGCACGTACTCGGATGGAAGCCGGTCTTG
TCGATCAGGATGATCTGGACGAAGAGCATCAGGGGCTCGCGCCAGCCG
AACTGTTCGCCAGGCTCAAGGCGAGCATGCCCGACGGCGAGGATCTCG
TCGTGACCCATGGCGATGCCTGCTTGCCGAATATCATGGTGGAAAATG
GCCGCTTTTCTGGATTCATCGACTGTGGCCGGCTGGGTGTGGCGGACC
GCTATCAGGACATAGCGTTGGCTACCCGTGATATTGCTGAAGAGCTTG
GCGGCGAATGGGCTGACCGCTTCCTCGTGCTTTACGGTATCGCCGCTC
CCGATTCGCAGCGCATCGCCTTCTATCGCCTTCTTGACGAGTTCTTCT
GAgggcccgtttaaacccgctgatcagcctcgactgtgccttctagtt -continued gccagccatctgttgtttgcccctcccccgtgccttccttgacccctgg
aaggtgccactcccactgtcctttcctaataaaatgaggaaattgcat
cgcattgtctgagtaggtgtcattctattctgggggtgggtgggc
aggacagcaaggggaggattgggaagacaatagcaggcatgctgggg
atgcggtgggctctatggcttctgaggcggaaagaaccagcatgtgag
caaaaggccagcaaaaggccaggaaccgtaaaaaggccgcgttgctgg
cgttttccataggctccgcccccctgacgagcatcacaaaaatcgac
gctcaagtcagaggtggcgaaacccgacaggactataaagataccagg
cgtttccccctggaagctccctcgtgcgctctcctgttccgaccctgc
cgcttaccggatacctgtccgcctttctcccttcgggaagcgtggcgc
tttctcatagctcacgctgtaggtatctcagttcggtgtaggtcgttc
gctccaagctgggctgtgtgcacgaaccccccgttcagcccgaccgct
gcgccttatccggtaactatcgtcttgagtccaacccggtaagacacg
acttatcgccactggcagcagccactggtaacaggattagcagagcga
ggtatgtaggcggtgctacagagttcttgaagtggtggcctaactacg
gctacactagaagaacagtatttggtatctgcgctctgctgaagccag
ttaccttcggaaaaagagttggtagctcttgatccggcaaacaaacca
ccgctggtagcggtggtttttttgtttgcaagcagcagattacgcgca
gaaaaaaggatctcaagaagatcctttgatcttttctacggggtctg
acgctcagtggaacgaaaactcacgttaagggattttggtcatttaa
ataccgctttccccgtcaagctctaaatcggggctcccctttagggt
tccgatttagtgctttacggcacctcgaccccaaaaaacttgattagg
gtgatggttcacgtagtgggccatcgccctgatagacggtttttcgcc
ctttgacgttggagtccacgttctttaatagtggactcttgttccaaa
ctggaacaacactcaaccctatctcggtctattcttttgatttataag
ggattttgccgatttcggcctattggttaaaaaatgagctgatttaac
aaaaatttaacgcgaattaattctgtggaatgtgtgtcagttagggtg
tggaaagtccccaggctccccagcaggcagaagtatgcaaagcacatt
ctagttgtggtttgtccaaactcatcaatgtatcttatcatgtctgta
taccgtcgacctctagctagagcttggcgtaatcatggtcatagctgt
ttcctgtgtgaaattgttatccgctcacaattccacacaacatacgag
ccggaagcataaagtgtaaagcctggggtgcctaatgagtgagctaac
tcacattaattgcgttgcgctcactgcccgctttccagtcgggaaacc
tgtcgtgccagctgcattaatgaatcggccaacgcgcggggagaggcg
gtttgcgtattgggcgctcttccgcttcctcgctcactgactcgctgc
gctcggtcgttcggctgcggcgagcggtatcagctcactcaaaggcgg
taatacggttatccacagaatcaggggataacgcaggaaagaacatgt
gagcaaaaggccagcaaaaggccaggaaccgtaaaaaggccgcgttgc
tggcgttttccataggctccgcccccctgacgagcatcacaaaaatc
gacgctcaagtcagaggtggcgaaacccgacaggactataaagatacc aggcgtttccccctggaagctccctcgtgcgctctcctgttccgaccc tgccgcttaccggatacctgtccgcctttctcccttcgggaagcgtgg cgctttctcatagctcacgctgtaggtatctcagttcggtgtaggtcg ttcgctccaagctgggctgtgtgcacgaaccccccgttcagcccgacc gctgcgccttatccggtaactatcgtcttgagtccaacccggtaagac acgacttatcgccactggcagcagccactggtaacaggattagcagag cgaggtatgtaggcggtgctacagagttcttgaagtggtggcctaact acggctacactagaagaacagtatttggtatctgcgctctgctgaagc cagttaccttcggaaaaagagttggtagctcttgatccggcaaacaaa ccaccgctggtagcggtttttttgtttgcaagcagcagattacgcgca gaaaaaaaggatctcaagaagatcctttgatcttttctacggggtctg acgctcagtggaacgaaaactcacgttaagggattttggtcatgagat tatcaaaaaggatcttcacctagatccttttaaattaaaaatgaagtt ttaaatcaatctaaagtatatatgagtaaacttggtctgacagttacc aatgcttaatcagtgaggcacctatctcagcgatctgtctatttcgtt catccatagttgcctgactccccgtcgtgtagataactacgatacggg agggcttaccatctggccccagtgctgcaatgataccgcgagacccac gctcaccggctccagatttatcagcaataaaccagccagccggaaggg ccgagcgcagaagtggtcctgcaactttatccgcctccatccagtcta ttaattgttgccgggaagctagagtaagtagttcgccagttaatagtt tgcgcaacgttgttgccattgctacaggcatcgtggtgtcacgctcgt cgtttggtatggcttcattcagctccggttcccaacgatcaaggcgag ttacatgatcccccatgttgtgcaaaaaagcggttagctccttcggtc ctccgatcgttgtcagaagtaagttggccgcagtgttatcactcatgg ttatggcagcactgcataattctcttactgtcatgccatccgtaagat gcttttctgtgactggtgagtactcaaccaagtcattctgagaatagt gtatgcggcgaccgagttgctcttgcccggcgtcaatacgggataata ccgcgccacatagcagaactttaaaagtgctcatcattggaaaacgtt cttcggggcgaaaactctcaaggatcttaccgctgttgagatccagtt cgatgtaacccactcgtgcacccaactgatcttcagcatcttttactt tcaccagcgtttctgggtgagcaaaaacaggaaggcaaaatgccgcaa aaaagggaataagggcgacacggaaatgttgaatactcatactcttcc tttttcaatattattgaagcatttatcagggttattgtctcatgagcg gatacatatttgaatgtatttagaaaaataaacaataggggttccgc gcacatttccccgaaaagtgccacctgacgtc 6.2. Helper Construct (total length of 7233 bp) (SEQ ID NO: 2)

gagttcgagcttgcatgcctgcaggtcgttacataacttacggtaaat ggcccgcctggctgaccgcccaacgacccccgcccattgacgtcaata atgacgtatgttcccatagtaacgccaatagggactttccattgacgt caatgggtggagtatttacggtaaactgcccacttggcagtacatcaa gtgtatcatatgccaagtacgccccctattgacgtcaatgacggtaaa tggcccgcctggcattatgcccagtacatgaccttatgggactttcct acttggcagtacatctacgtattagtcatcgctattaccatggtgatg cggttttggcagtacatcaatgggcgtggatagcggtttgactcacgg ggatttccaagtctccaccccattgacgtcaatgggagtttgttttgg caccaaaatcaacgggactttccaaaatgtcgtaacaactccgcccca ttgacgcaaatgggcggtaggcgtgtacggtgggaggtctatataagc agagctcgtttagtgaaccgtcagatcgcctggagacgccatccacgc tgttttgacctccatagaagacaccgggaccgatccagcctccggact ctagaggatccggtactagaggaactgaaaaaccagaaagttaactgg taagtttagtcttttgtcttttatttcaggtcccggatccggtggtg gtgcaaatcaaagaactgctcctcagtggatgttgcctttacttctag gcctgtacggaagtgttacttctgctctaaaagctgcggaattgtacc cgcgggccaccatggcatcaatgcagaagctgatctcagaggaggac ctgcttatggccatggaggcccgaattctgcagatggataaaATGGGT

AGTTCTTTAGACGATGAGCATATCCTCTCTGCTCTTCTGCAAAGCGAT

GACGAGCTTGTTGGTGAGGATTCTGACAGTGAAATATCAGATCACGTA

AGTGAAGATGACGTCCAGAGCGATACAGAAGAAGCGTTTATAGATGAG

GTACATGAAGTGCAGCCAACGTCAAGCGGTAGTGAAATATTAGACGAA

CAAAATGTTATTGAACAACCAGGTTCTTCATTGGCTTCTAACAGAATC

TTGACCTTGCCACAGAGGACTATTAGAGGTAAGAATAAACATTGTTGG

TCAACTTCAAAGTCCACGAGGCGTAGCCGAGTCTCTGCACTGAACATT

GTCAGATCTCAAAGAGGTCCGACGCGTATGTGCCGCAATATATATGAC

CCACTTTTATGCTTCAAACTATTTTTTACTGATGAGATAATTTCGGAA

ATTGTAAAATGGACAAATGCTGAGATATCATTGAAACGTCGGGAATCT

ATGACAGGTGCTACATTTCGTGACACGAATGAAGATGAAATCTATGCT

TTCTTTGGTATTCTGGTAATGACAGCAGTGAGAAAAGATAATCACATG

TCCACAGATGACCTCTTTGATCGATCTTTGTCAATGGTGTACGTCTCT

GTAATGAGTCGTGATCGTTTTGATTTTTTGATACGATGTCTTAGAATG

GATGACAAAAGTATACGGCCCACACTTCGAGAAAACGATGTATTTACT

CCTGTTAGAAAAATATGGGATCTCTTTATCCATCAGTGCATACAAAAT

TACACTCCAGGGGCTCATTTGACCATAGATGAACAGTTACTTGGTTTT

AGAGGACGGTGTCCGTTTAGGATGTATATCCCAAACAAGCCAAGTAAG

TATGGAATAAAAATCCTCATGATGTGTGACAGTGGTACGAAGTATATG

ATAAATGGAATGCCTTATTTGGGAAGAGGAACACAGACCAACGGAGTA

CCACTCGGTGAATACTACGTGAAGGAGTTATCAAAGCCTGTGCACGGT

AGTTGTCGTAATATTACGTGTGACAATTGGTTCACCTCAATCCCTTTG

GCAAAAAACTTACTACAAGAACCGTATAAGTTAACCATTGTGGGAACC

GTGCGATCAAACAAACGCGAGATACCGGAAGTACTGAAAAACAGTCGC

TCCAGGCCAGTGGGAACATCGATGTTTTGTTTTGACGGACCCCCTTACT

-continued

CTCGTCTCATATAAACCGAAGCCAGCTAAGATGGTATACTTATTATCA
TCTTGTGATGAGGATGCTTCTATCAACGAAAGTACCGGTAAACCGCAA
ATGGTTATGTATTATAATCAAACTAAAGGCGGAGTGGACACGCTAGAC
CAAATGTGTTCTGTGATGACCTGCAGTAGGAAGACGAATAGGTGGCCT
ATGGCATTATTGTACGGAATGATAAACATTGCCTGCATAAATTCTTTT
ATTATATACAGCCATAATGTCAGTAGCAAGGGAGAAAAGGTCCAAAGT
CGCAAAAAATTTATGAGAAACCTTTACATGAGCCTGACGTCATCGTTT
ATGCGTAAGCGTTTAGAAGCTCCTACTTTGAAGAGATATTTGCGCGAT
AATATCTCTAATATTTTGCCAAATGAAGTGCCTGGTACATCAGATGAC
AGTACTGAAGAGCCAGTAATGAAAAAACGTACTTACTGTACTTACTGC
CCCTCTAAAATAAGGCGAAAGGCAAATGCATCGTGCAAAAAATGCAAA
AAAGTTATTTGTCGAGAGCATAATATTGATATGTGCCAAAGTTGTTTC
TGActgactaataagtataatttgtttctattatgtataagttaagct
aattaggatcatccagcacagtggcggccgccgcggcgtacgaggcct
gcatgctccggacctgcaggttcgaagtcgacagatctcaattgggc
ccctatagtgtcacctaaataattccgcccccccctctccctccccc
ccctaacgttactggccgaagccgcttggaataaggccggtgtgcgt
ttgtctatatgttattttccaccatattgccgtcttttggcaatgtga
gggcccggaaacctggccctgtcttcttgacgagcattcctaggggtc
tttcccctctcgccaaaggaatgcaaggtctgttgaatgtcgtgaagg
aagcagttcctctggaagcttcttgaagacaaacaacgtctgtagcga
ccctttgcaggcagcggaaccccccacctggcgacaggtgcctctgcg
gccaaaagccacgtgtataagatacacctgcaaaggcggcacaacccc
agtgccacgttgtgagttggatagttgtggaaagagtcaaatggctct
cctcaagcgtattcaacaagggctgaaggatgcccagaaggtacccc
attgtatgggatctgatctggggcctcggtgcacatgctttacatgtg
tttagtcgaggttaaaaaaacgtctaggcccccccgaaccacggggacg
tggttttcctttgaaaaacacgatgataatATGGCCACAACCATGGTG
AGCAAGGGCGAGGAGCTGTTCACCGGGGTGGTGCCCATCCTGGTCGAG
CTGGACGGCGACGTAAACGGCCACAAGTTCAGCGTGTCCGGCGAGGGC
GAGGGCGATGCCACCTACGGCAAGCTGACCCTGAAGTTCATCTGCACC
ACCGGCAAGCTGCCCGTGCCCTGGCCCACCCTCGTGACCACCCTGACC
TACGGCGTGCAGTGCTTCAGCCGCTACCCCGACCACATGAAGCAGCAC
GACTTCTTCAAGTCCGCCATGCCCGAAGGCTACGTCCAGGAGCGCACC
ATCTTCTTCAAGGACGACGGCAACTACAAGACCCGCGCCGAGGTGAAG
TTCGAGGGCGACACCCTGGTGAACCGCATCGAGCTGAAGGGCATCGAC
TTCAAGGAGGACGGCAACATCCTGGGGCACAAGCTGGAGTACAACTAC
AACAGCCACAACGTCTATATCATGGCCGACAAGCAGAAGAACGGCATC
AAGGTGAACTTCAAGATCCGCCACAACATCGAGGACGGCAGCGTGCAG
CTCGCCGACCACTACCAGCAGAACACCCCCATCGGCGACGGCCCCGTG -continued CTGCTGCCCGACAACCACTACCTGAGCACCCAGTCCGCCCTGAGCAAA
GACCCCAACGAGAAGCGCGATCACATGGTCCTGCTGGAGTTCGTGACC
GCCGCCGGGATCACTCTCGGCATGGACGAGCTGTACAAGTAAagcggc
ccgataaaataaaagatttttatttagtctccagaaaaagggggaatg
aaagaccccacctgtaggtttggcaagctagcttaagtaacgccatt
tgcaaggcatggaaaatacataactgagaatagagaagttcagatcaa
ggttaggaacagagagacagcagaatatgggccaaacaggatggccgc
ggggatccagacatgataagatacattgatgagtttggacaaaccaca
actagaatgcagtgaaaaaaatgctttatttgtgaaatttgtgatgct
attgctttatttgtaaccattataagctgcaataaacaagttaacaac
aacaattgcattcattttatgtttcaggttcaggggaggtgtgggag
gttttttcggatcctctagagtcgatctgcaggcatgctagcttggcg
taatcatggtcatagctgtttcctgtgtgaaattgttatccgctcaca
attccacacaacatacgagccggaagcataaagtgtaaagcctggggt
gcctaatgagtgagctaactcacattaattgcgttgcgctcactgccc
gctttccagtcgggaaacctgtcgtgccagctgcattaatgaatcggc
caacgcgcggggagaggcggtttgcgtattgggcgctcttccgcttcc
tcgctcactgactcgctgcgctcggtcgttcggctgcggcgagcggta
tcagctcactcaaaggcggtaatacggttatccacagaatcaggggat
aacgcaggaaagaacatgtgagcaaaaggccagcaaaaggccaggaac
cgtaaaaaggccgcgttgctggcgtttttccataggctccgcccccct
gacgagcatcacaaaaatcgacgctcaagtcagaggtggcgaaacccg
acaggactataaagataccaggcgtttccccctggaagctccctcgtg
cgctctcctgttccgaccctgccgcttaccggatacctgtccgccttt
ctcccttcgggaagcgtggcgctttctcatagctcacgctgtaggtat
ctcagttcggtgtaggtcgttcgctccaagctgggctgtgtgcacgaa
ccccccgttcagcccgaccgctgcgccttatccggtaactatcgtctt
gagtccaacccggtaagacacgacttatcgccactggcagcagccact
ggtaacaggattagcagagcgaggtatgtaggcggtgctacagagttc
ttgaagtggtggcctaactacggctacactagaaggacagtatttggt
atctgcgctctgctgaagccagttaccttcggaaaaagagttggtagc
tcttgatccggcaaacaaaccaccgctggtagcggtggtttttttgtt
tgcaagcagcagattacgcgcagaaaaaaaggatctcaagaagatcct
ttgatcttttctacggggtctgacgctcagtggaacgaaaactcacgt
taagggattttggtcatgagattatcaaaaaggatcttcacctagatc
cttttaaattaaaaatgaagttttaaatcaatctaaagtatatatgag
taaacttggtctgacagttaccaatgcttaatcagtgaggcacctatc
tcagcgatctgtctatttcgttcatccatagttgcctgactccccgtc
gtgtagataactacgatacgggagggcttaccatctggccccagtgct
gcaatgataccgcgagacccacgctcaccggctccagatttatcagca
ataaaccagccagccggaagggccgagcgcagaagtggtcctgcaact -continued

```
ttatccgcctccatccagtctattaattgttgccgggaagctagagta
agtagttcgccagttaatagtttgcgcaacgttgttgccattgctaca
ggcatcgtggtgtcacgctcgtcgtttggtatggcttcattcagctcc
ggttcccaacgatcaaggcgagttacatgatcccccatgttgtgcaaa
aaagcggttagctccttcggtcctccgatcgttgtcagaagtaagttg
gccgcagtgttatcactcatggttatggcagcactgcataattctctt
actgtcatgccatccgtaagatgcttttctgtgactggtgagtactca
accaagtcattctgagaatagtgtatgcggcgaccgagttgctcttgc
ccggcgtcaatacgggataataccgcgccacatagcagaactttaaaa
gtgctcatcattggaaaacgttcttcggggcgaaaactctcaaggatc
ttaccgctgttgagatccagttcgatgtaacccactcgtgcacccaac
tgatcttcagcatcttttactttcaccagcgtttctgggtgagcaaaa
acaggaaggcaaaatgccgcaaaaaagggaataagggcgacacggaaa
tgttgaatactcatactcttccttttcaatattattgaagcatttat
cagggttattgtctcatgagcggatacatatttgaatgtatttagaaa
aataaacaaatagggggttccgcgcacatttccccgaaaagtgccacct
gacgtctaagaaaccattattatcatgacattaacctataaaaatagg
cgtatcacgaggccctttcgtctcgcgcgtttcggtgatgacggtgaa
aacctctgacacatgcagctcccggagacggtcacagcttgtctgtaa
gcggatgccgggagcagacaagcccgtcagggcgcgtcagcgggtgtt
ggcgggtgtcggggctggcttaactatgcggcatcagagcagattgta
ctgagagtgcaccatatgcggtgtgaaataccgcacagatgcgtaagg
agaaaataccgcatcaggcgccattcgccattcaggctgcgcaactgt
tgggaagggcgatcggtgcgggcctcttcgctattacgccagctggcg
aaaggggggatgtgctgcaaggcgattaagttgggtaacgccagggttt
cccagtcacgacgttgtaaaacgacggccagt
```

6.3. Reporter System (total length of 6054 bp) (SEQ ID NO: 3)

```
GAGTTCGAGCTTGCATGCCggataTCCGGCGCTCGCTAGAGTCTCCGC
TCGGAGGACAGTACTCCGCTCGGAGGACAGTACTCCGCTCGGAGGACA
GTACTCCGCTCGGAGGACAGTACTCCGCTCGGAGGACAGTACTCCGAC
CTGCAGGCATGGAAGCTTGGATCagggtatataatgggagctcGTTTA
GTGAACCGTCAGATCGCCTGGAGACGCCATCCACGCTGTTTTGACCTC
CATAGAAGACACCGGGACCGATCCAGCCTCCGGACTCTAGAGGATCCG
GTACTAGAGGAACTGAAAACCAGAAAGTTAACTGGTAAGTTTAGTCT
TTTTGTCTTTTATTTCAGGTCCCGGATCCGGTGGTGGTGCAAATCAAA
GAACTGCTCCTCAGTGGATGTTGCCTTTACTTCTAGGCCTGTACGGAA
GTGTTACTTCTGCTCTAAAAGCTGCGGAATTGTACCCGCGGGCCCACC
ATGGCATCAATGCAGAAGCTGATCTCAGAGGAGGACCTGCTTATGGCC
ATGGAGGCCCgaattcccATGGCTAGCAAAGGAGAAGAACTTTTCACT
GGAGTTGTCCCAATTCTTGTTGAATTAGATGGTGATGTTAATGGGCAC
AAATTTTCTGTCAGTGGAGAGGGTGAAGGTGATGCTACATACGGAAAG
CTTACCCTTAAATTTATTTGCACTACTGGAAAACTACCTGTTCCATGG
CCAACACTTGTCACTACTTTCTCTTATGGTGTTCAATGCTTTTCCCGT
TATCCGGATCATATGAAACGGCATGACTTTTTCAAGAGTGCCATGCCC
GAAGGTTATGTACAGGAACGCACTATATCTTTCAAAGATGACGGGAAC
TACAAGACGCGTGCTGAAGTCAAGTTTGAAGGTGATACCCTTGTTAAT
CGTATCGAGTTAAAAGGTATTGATTTTAAAGAAGATGGAAACATTCTC
GGACACAAACTCGAGTACAACTATAACTCACACAATGTATACATCACG
GCAGACAAACAAAGAATGGAATCAAAGCTAACTTCAAAATTCGCCAC
AACATTGAAGATGGATCCGTTCAACTAGCAGACCATTATCAACAAAAT
ACTCCAATTGGCGATGGCCCTGTCCTTTTACCAGACAACCATTACCTG
TCGACACAATCTGCCCTTTCGAAAGATCCCAACGAAAAGCGTGACCAC
ATGGTCCTTCTTGAGTTTGTAACTGCTGCTGGGATTACACATGGCATG
GATGCCAAGTTGACCAGTGCCGTTCCGGTGCTCACCGCGCGCGACGTC
GCCGGAGCGGTCGAGTTCTGGACCGACCGGCTCGGGTTCTCCCGGGAC
TTCGTGGAGGACGACTTCGCCGGTGTGGTCCGGGACGACGTGACCCTG
TTCATCAGCGCGGTCCAGGACCAGGTGGTGCCGGACAACACCCTGGCC
TGGGTGTGGGTGCGCGGCCTGGACGAGCTGTACGCCGAGTGGTCGGAG
GTCGTGTCCACGAACTTCCGGGACGCCTCCGGGCCGGCCATGACCGAG
ATCGGCGAGCAGCCGTGGGGCGGGAGTTCGCCCTGCGCGACCCGGCC
GGCAACTGCTGCACTTCGTGGCCGAGGAGCAGGACTGAtaattgact
agagatctcaattggggcccctatagtgtcacctaaataattccgccc
cccctctccctccccccccctaacgttactggccgaagccgcttgg
aataaggccggtgtgcgttttgtctatatgttatttccaccatattgc
cgtcttttggcaatgtgagggcccggaaacctggccctgtcttcttga
cgagcattcctagggggtctttcccctctcgccaaaggaatgcaaggtc
tgttgaatgtcgtgaaggaagcagttcctctggaagcttcttgaagac
aaacaacgtctgtagcgaccctttgcaggcagcggaaccccccaccctg
gcgacaggtgcctctgcggccaaaagccacgtgtataagatacacctg
caaaggcggcacaaccccagtgccacgttgtgagttggatagttgtgg
aaagagtcaaatggctctcctcaagcgtattcaacaaggggctgaagg
atgcccagaaggtaccccattgtatgggatctgatctggggcctcggt
gcacatgctttacatgtgtttagtcgaggttaaaaaaacgtctaggcc
ccccgaaccacggggacgtggttttccttttgaaaaaacacgatgataat
ATGGCCACAACCATGGTGAGCAAGGGCGAGGAGCTGTTCACCGGGGTG
GTGCCCATCCTGGTCGAGCTGGACGGCGACGTAAACGGCCACAAGTTC
AGCGTGTCCGGCGAGGGCGAGGGCGATGCCACCTACGGCAAGCTGACC
CTGAAGTTCATCTGCACCACCGGCAAGCTGCCCGTGCCCTGGCCCACC
CTCGTGACCACCCTGACCTACGGCGTGCAGTGCTTCAGCCGCTACCCC
```

```
GACCACATGAAGCAGCACGACTTCTTCAAGTCCGCCATGCCCGAAGGC
TACGTCCAGGAGCGCACCATCTTCTTCAAGGACGACGGCAACTACAAG
ACCCGCGCCGAGGTGAAGTTCGAGGGCGACACCCTGGTGAACCGCATC
GAGCTGAAGGGCATCGACTTCAAGGAGGACGGCAACATCCTGGGGCAC
AAGCTGGAGTACAACTACAACAGCCACAACGTCTATATCATGGCCGAC
AAGCAGAAGAACGGCATCAAGGTGAACTTCAAGATCCGCCACAACATC
GAGGACGGCAGCGTGCAGCTCGCCGACCACTACCAGCAGAACACCCCC
ATCGGCGACGGCCCCGTGCTGCTGCCCGACAACCACTACCTGAGCACC
CAGTCCGCCCTGAGCAAAGACCCCAACGAGAAGCGCGATCACATGGTC
CTGCTGGAGTTCGTGACCGCCGCCGGGATCACTCTCGGCATGGACGAG
CTGTACAAGTAAagcggcccgataaaataaaagattttatttagtctc
cagaaaagggggaatgaaagaccccacctgtaggtttggcaagcta
gcttaagtaacgccattttgcaaggcatggaaaatacataactgagaa
tagagaagttcagatcaaggttaggaacagagagacagcagaatatgg
gccaaacaggatCGCGGCCGCGGGGATCCAGACATGATAAGATACATT
GATGAGTTTGGACAAACCACAACTAGAATGCAGTGAAAAAAATGCTTT
ATTTGTGAAATTTGTGATGCTATTGCTTTATTTGTAACCATTATAAGC
TGCAATAAACAAGTTAACAACAACAATTGCATTCATTTTATGTTTCAG
GTTCAGGGGAGGTGTGGGAGGTTTTTTCGGATCCTCTAGAGTCGATC
TGCAGGCATGCTAGCTTGGCGTAATCATGGTCATAGCTGTTTCCTGTG
TGAAATTGTTATCCGCTCACAATTCCACACAACATACGAGCCGGAAGC
ATAAAGTGTAAAGCCTGGGGTGCCTAATGAGTGAGCTAACTCACATTA
ATTGCGTTGCGCTCACTGCCCGCTTTCCAGTCGGGAAACCTGTCGTGC
CAGCTGCATTAATGAATCGGCCAACGCGCGGGGAGAGGCGGTTTGCGT
ATTGGGCGCTCTTCCGCTTCCTCGCTCACTGACTCGCTGCGCTCGGTC
GTTCGGCTGCGGCGAGCGGTATCAGCTCACTCAAAGGCGGTAATACGG
TTATCCACAGAATCAGGGGATAACGCAGGAAAGAACATGTGAGCAAAA
GGCCAGCAAAAGGCCAGGAACCGTAAAAAGGCCGCGTTGCTGGCGTTT
TTCCATAGGCTCCGCCCCCCTGACGAGCATCACAAAAATCGACGCTCA
AGTCAGAGGTGGCGAAACCCGACAGGACTATAAAGATACCAGGCGTTT
CCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCC
AAGCTGGGCTGTGTGCACGAACCCCCCGTTCAGCCCGACCGCTGCGCC
TTATCCGGTAACTATCGTCTTGAGTCCAACCCGGTAAGACACGACTTA
TCGCCACTGGCAGCAGCCACTGGTAACAGGATTAGCAGAGCGAGGTAT
GTAGGCGGTGCTACAGAGTTCTTGAAGTGGTGGCCTAACTACGGCTAC
ACTAGAAGGACAGTATTTGGTATCTGCGCTCTGCTGAAGCCAGTTACC
TTCGGAAAAAGAGTTGGTAGCTCTTGATCCGGCAAACAAACCACCGCT
GGTAGCGGTGGTTTTTTTGTTTGCAAGCAGCAGATTACGCGCAGAAAA
AAAGGATCTCAAGAAGATCCTTTGATCTTTTCTACGGGGTCTGACGCT
CAGTGGAACGAAAACTCACGTTAAGGGATTTTGGTCATGAGATTATCA
AAAAGGATCTTCACCTAGATCCTTTTAAATTAAAAATGAAGTTTTAAA
TCAATCTAAAGTATATATGAGTAAACTTGGTCTGACAGTTACCAATGC
TTAATCAGTGAGGCACCTATCTCAGCGATCTGTCTATTTCGTTCATCC
ATAGTTGCCTGACTCCCCGTCGTGTAGATAACTACGATACGGGAGGGC
TTACCATCTGGCCCCAGTGCTGCAATGATACCGCGAGACCCACGCTCA
CCGGCTCCAGATTTATCAGCAATAAACCAGCCAGCCGGAAGGGCCGAG
CGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGC
AACGTTGTTGCCATTGCTACAGGCATCGTGGTGTCACGCTCGTCGTTT
GGTATGGCTTCATTCAGCTCCGGTTCCCAACGATCAAGGCGAGTTACA
TGATCCCCCATGTTGTGCAAAAAAGCGGTTAGCTCCTTCGGTCCTCCG
ATCGTTGTCAGAAGTAAGTTGGCCGCAGTGTTATCACTCATGGTTATG
GCAGCACTGCATAATTCTCTTACTGTCATGCCATCCGTAAGATGCTTT
TCTGTGACTGGTGAGTACTCAACCAAGTCATTCTGAGAATAGTGTATG
CGGCGACCGAGTTGCTCTTGCCCGGCGTCAATACGGGATAATACCGCG
CCACATAGCAGAACTTTAAAAGTGCTCATCATTGGAAAACGTTCTTCG
GGGCGAAAACTCTCAAGGATCTTACCGCTGTTGAGATCCAGTTCGATG
TAACCCACTCGTGCACCCAACTGATCTTCAGCATCTTTTACTTTCACC
AGCGTTTCTGGGTGAGCAAAAACAGGAAGGCAAAATGCCGCAAAAAAG
GGAATAAGGGCGACACGGAAATGTTGAATACTCATACTCTTCCTTTTT
CAATATTATTGAAGCATTTATCAGGGTTATTGTCTCATGAGCGGATAC
ATATTTGAATGTATTTAGAAAAATAAACAAATAGGGGTTCCGCGCACA
TTTCCCCGAAAAGTGCCACCTGACGTCTAAGAAACCATTATTATCATG
ACATTAACCTATAAAAATAGGCGTATCACGAGGCCCTTTCGTCTCGCG
CGTTTCGGTGATGACGGTGAAAACCTCTGACACATGCAGCTCCCGGAG
ACGGTCACAGCTTGTCTGTAAGCGGATGCCGGGAGCAGACAAGCCCGT
CAGGGCGCGTCAGCGGGTGTTGGCGGGTGTCGGGGCTGGCTTAACTAT
GCGGCATCAGAGCAGATTGTACTGAGAGTGCACCATATGCGGTGTGAA
ATACCGCACAGATGCGTAAGGAGAAAATACCGCATCAGGCGCCATTCG
CCATTCAGGCTGCGCAACTGTTGGGAAGGGCGATCGGTGCGGGCCTCT
TCGCTATTACGCCAGCTGGCGAAAGGGGGATGTGCTGCAAGGCGATTA
AGTTGGGTAACGCCAGGGTTTTCCCAGTCACGACGTTGTAAAACGACG
GCCAGT
```

What is claimed is:

1. A method of performing gene modification under a drug-free environment in a trapped mammalian stem cell library by trapper constructs and helper constructs, which comprises:
   (a) introducing piggyBac transposon into the trapped mammalian stem cell library by introducing (i) a trapper construct; (ii) a helper construct and (iii) a dual reporter construct, wherein the trapper construct comprises the piggyBac terminal inverted repeats with 122 nucleotides and a sequence of an internal ribosomal entry site (IRES) and, wherein the helper construct comprises an IRES linking both of transposases and a first fluorescent protein coding sequence driven by a human cytomegalovirus promoter for targeting silent genes or repressed genes in silenced loci to separate said silent genes or said repressed genes with low-level expression, and (iii) the dual reporter construct to verify said silent genes or said repressed genes with low-level expression in said trapped mammalian stem cells, wherein said dual reporter construct comprises two copies of a second fluorescent protein coding and being under a control of yeast upstream activation sequence and an E1b minimal promoter, wherein the trapper construct has the nucleotide sequence as set forth in SEQ ID NO: 1;
   (b) culturing the transfected cells;
   (c) cloning and separating the first fluorescent protein positive cells harboring the helper construct separated from the first fluorescent protein negative cells;
   (d) collecting under a drug-free selection the first fluorescent protein negative cells exhibiting silent gene expression or repressed gene expression;
   (e) verifying the presence or absence of the second fluorescent protein and separating the second fluorescent positive cells from the second fluorescent negative cells, wherein the second fluorescent positive cells exhibit active gene expression and the second I fluorescent negative cells exhibit silent or repressed expression; and
   (f) collecting the second fluorescent positive cells exhibiting active gene expression and the second fluorescent negative cells exhibiting silent gene expression, wherein said silent genes or said repressed genes trapped bear the piggyBac terminal.

2. A method of performing gene modification under a drug-free environment in a trapped mammalian cell library by trapper constructs and helper constructs, which comprises:
   (a) introducing piggyBac transposon into the trapped mammalian cell library by introducing (i) a trapper construct; (ii) a helper construct and (iii) a dual reporter construct, wherein the trapper construct comprises the piggyBac terminal inverted repeats with 122 nucleotides and a sequence of an internal ribosomal entry site (IRES) and, wherein the helper construct comprises an IRES linking both of transposases and a first fluorescent protein coding sequence driven by a human cytomegalovirus promoter for targeting silent genes or repressed genes in silenced loci to separate said silent genes or said repressed genes with low-level expression, and (iii) the dual reporter construct to verify said silent genes or said repressed genes with low-level expression in said trapped mammalian cells, wherein said dual reporter construct comprises two copies of a second fluorescent protein coding and being under a control of yeast upstream activation sequence and an E1b minimal promoter, wherein the trapper construct has the nucleotide sequence as set forth in SEQ ID NO: 1;
   (b) culturing the transfected cells;
   (c) cloning and separating the first fluorescent protein positive cells harboring the helper construct separated from the first fluorescent protein negative cells;
   (d) collecting under a drug-free selection the first fluorescent protein negative cells exhibiting silent gene expression or repressed gene expression;
   (e) verifying the presence or absence of the second fluorescent protein and separating the second fluorescent positive cells from the second fluorescent negative cells, wherein the second fluorescent positive cells exhibit active gene expression and the second fluorescent negative cells exhibit silent or repressed expression; and
   (f) collecting the second fluorescent positive cells exhibiting active gene expression and the second fluorescent negative cells exhibiting silent gene expression, wherein said silent genes or said repressed genes trapped bear the piggyBac terminal.

3. The method of performing gene modification of claim 2, wherein the helper construct has the nucleotide sequence as set forth in SEQ ID NO: 2.

4. The method of performing gene modification of claim 2, wherein an insertion rate of more than 91% is achieved.

* * * * *